(12) United States Patent
Wolfe et al.

(10) Patent No.: US 10,849,539 B2
(45) Date of Patent: Dec. 1, 2020

(54) SENSOR INSERTION

(71) Applicant: PercuSense, Inc., Valencia, CA (US)

(72) Inventors: Katherine Wolfe, Mississauga (CA);
Joseph Ferreira, Seattle, WA (US);
Ellen Messer, Pasadena, CA (US);
Rajiv Shah, Rancho Palos Verdes, CA (US); Konrad Chan, Pasadena, CA (US)

(73) Assignee: PercuSense, Inc., Valencia, CA (US)

( * ) Notice: Subject to any disclaimer, the term of this patent is extended or adjusted under 35 U.S.C. 154(b) by 252 days.

(21) Appl. No.: 15/816,549

(22) Filed: Nov. 17, 2017

(65) Prior Publication Data
US 2018/0279926 A1  Oct. 4, 2018

Related U.S. Application Data

(60) Provisional application No. 62/477,942, filed on Mar. 28, 2017, provisional application No. 62/521,985, filed on Jun. 19, 2017, provisional application No. 62/524,416, filed on Jun. 23, 2017, provisional application No. 62/568,293, filed on Oct. 4, 2017, provisional application No. 62/568,432, filed on Oct. 5, 2017.

(51) Int. Cl.
*A61B 5/145* (2006.01)
*A61B 5/1473* (2006.01)
*A61B 5/00* (2006.01)
*A61B 17/34* (2006.01)

(52) U.S. Cl.
CPC ............ *A61B 5/1473* (2013.01); *A61B 5/145* (2013.01); *A61B 5/14503* (2013.01); *A61B 5/14532* (2013.01); *A61B 5/6833* (2013.01); *A61B 17/3468* (2013.01); *A61B 17/3496* (2013.01); *A61B 2017/3492* (2013.01); *A61B 2560/0214* (2013.01); *A61B 2560/0412* (2013.01); *A61B 2560/063* (2013.01)

(58) Field of Classification Search
CPC . A61B 5/145; A61B 5/14503; A61B 5/14532; A61B 5/6833; A61B 5/1473
See application file for complete search history.

(56) References Cited

U.S. PATENT DOCUMENTS

| | | | |
|---|---|---|---|
| 9,980,670 B2 * | 5/2018 | Funderburk | A61B 5/14532 |
| 2007/0173706 A1 | 7/2007 | Neinast | |
| 2012/0265042 A1 * | 10/2012 | Neinast | A61B 5/14532 600/347 |
| 2015/0289788 A1 * | 10/2015 | Simpson | A61B 5/14532 600/345 |
| 2016/0331284 A1 | 11/2016 | Pace | |
| 2019/0117256 A1 * | 4/2019 | Jager | A61B 5/14865 |

FOREIGN PATENT DOCUMENTS

| | | |
|---|---|---|
| WO | 2005/044116 | 5/2005 |
| WO | 2007/058921 | 5/2007 |
| WO | 2016/183493 | 11/2016 |

* cited by examiner

*Primary Examiner* — Eric J Messersmith
(74) *Attorney, Agent, or Firm* — PercuSense, Inc.

(57) ABSTRACT

An on-body insertion system is described. The on-body system includes a sensor in a first position being substantially parallel to an insertion surface. Activation of an actuator transitions the sensor to a second position. Wherein the transition imparts movement to the sensor that is substantially parallel to the insertion surface and the second position results in the sensing area being beneath the insertion surface.

20 Claims, 18 Drawing Sheets

SENSOR INSERTION

RELATED APPLICATIONS

This application claims the benefit of U.S. provisional application No. 62/477,942, filed on Mar. 28, 2017; 62/521,985, filed on Jun. 19, 2017; 62/524,416 filed on Jun. 23, 2017; 62/568,293, filed on Oct. 4, 2017; and 62/568,432, filed on Oct. 5, 2017. The applications listed above are hereby incorporated by reference in their entireties for all purposes.

FIELD OF THE INVENTION

The present invention is generally directed to insertion of devices that perform in vivo monitoring of at least one physiological parameter such as, but not limited to, perfusion, temperature or concentration of at least one analyte. In particular, minimally invasive insertion or placement of electrochemical sensors that provide real-time information regarding the presence or concentration of an analyte or analytes like glucose, oxygen or lactate within a subject.

BACKGROUND OF THE INVENTION

Insertion systems that place sensors in subcutaneous tissue often seem like a study in contradictions because sensors carefully designed to minimize insertion volume utilize large cumbersome insertion tools that frequently require two-hands. The components typically utilized with many insertion techniques include the sensor having an adhesive patch to secure the sensor to the subject, some type of electronics package to provide power and communications to the sensor, and an insertion tool or insertion aid that assists in driving the sensor into the subcutaneous space. With some systems, a supplemental adhesive patch or over-tape may be necessary to secure the sensor and electronics package to the skin of a subject.

Commonly, a sensor is coupled to an insertion tool that includes a needle that will drive the sensor to a preferred insertion depth. While attached to the insertion tool, liners are removed to expose adhesive that will attach the sensor to the subject. The sensor is inserted into the subject and the insertion tool is separated from the sensor. With some systems the needle is retracted into the insertion tool while other systems require manual removal of the needle after the insertion tool is removed. In both cases, shortly after insertion, the needle must be properly disposed of as medical waste. Typically, after removal of the insertion tool the electronics package must still be secured to the sensor. With some insertion systems, after the electronics package is secured to the sensor, it is advised to apply an additional adhesive layer to secure the combined electronics package and sensor to the skin.

Not only do these systems complicate insertion with multiple steps for insertion and connection of the electronics package, repeated handling and manipulation of the insertion site can adversely affect sensor performance. The claimed invention seeks to address many of the issues discussed above regarding insertion techniques or systems. In many examples discussed below elements, features, and actions should not be construed to be restricted to a single embodiment being discussed. Where possible, the elements, features and actions discussed below should be construed as applicable across all the different embodiments.

BRIEF SUMMARY OF THE INVENTION

In one embodiment an on-body insertion system is described. The on-body system includes a sensor in a first position having a distal end being substantially parallel to an insertion surface. Activation of an actuator transitions the sensor to a second position. Wherein the transition imparts movement to the sensor that is substantially parallel to the insertion surface and the second position results in the sensing area being beneath the insertion surface.

In another embodiment, a method of inserting a sensor assembly is described. The method includes an operation that activates an actuator to release the sensor assembly from a first position. In another operation, a proximal end of the sensor assembly traverses from the first position to a second position, the traversing being substantially parallel to the insertion surface. Wherein a distal end of the sensor assembly is inserted below the insertion surface when the proximal end of the sensor assembly is in the second position.

Other features and advantages of the invention will become apparent from the following detailed description, taken in conjunction with the accompanying drawings which illustrate, by way of example, various features of embodiments of the invention.

DETAILED DESCRIPTION

Sensor insertion techniques are often heavily influenced by the techniques used to manufacture the sensor. For example, constructing a sensor on a rigid substrate may require the sensor to be protected within a needle to prevent unintentional flexing or bending. With a sensor designed to be made on a flexible substrate, insertion techniques can be employed that simplify insertion, while reducing both the on-body footprint and overall volume of the insertion system.

Figure 1:
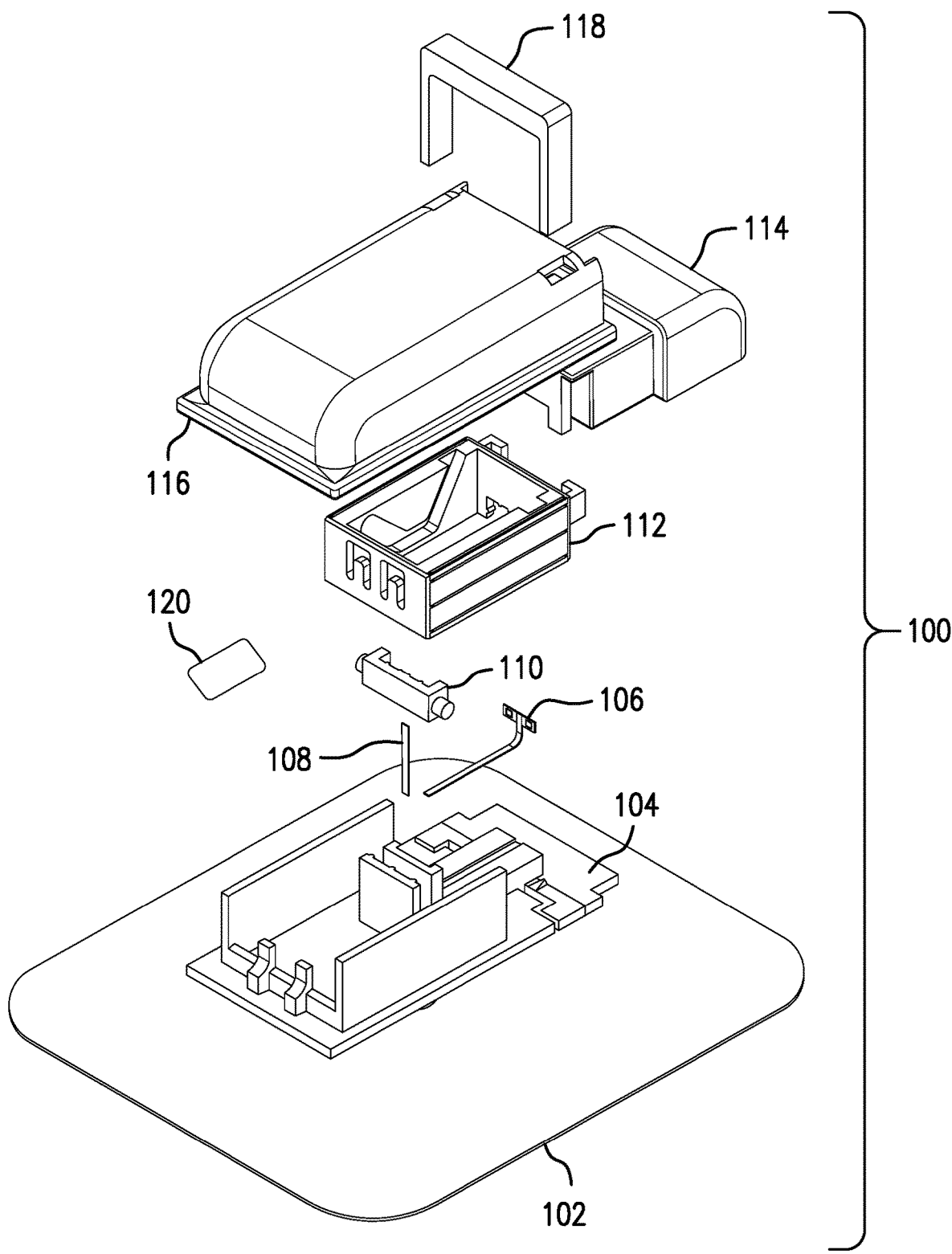
FIG. 1 is an exploded isometric view of an on-body system.

FIG. 1 is an exploded isometric view of an on-body system 100, in accordance with an exemplary embodiment of the present invention. The on-body system 100 is intended to achieve insertion and operation of a sensor 106. In many embodiments, the sensor 106, or sensor assembly 106, is at least partially based on the disclosure made in U.S. patent application Ser. No. 15/472,194, filed on Mar. 28, 2017 along with U.S. patent application Ser. No. 15/455,155, filed on Mar. 9, 2017, which are herein incorporated by reference in their entirety.

In addition to the sensor assembly 106 the embodiments of the on-body system 100 includes components such as a patch 102, a chassis 104, a sharp 108, a sharp carrier 110, a carriage 112, an electronics module 114, a cover 116, an actuator 118, and energy storage 120. Features of the individual components listed above, along with how particular components interact with each other is described in further detail below. Note that the various embodiments discussed throughout this disclosure are intended to be exemplary and should not be construed as limiting. Furthermore, elements, components, and features discussed regarding a particular embodiment should, where possible, be construed as interchangeable or capable of being implemented with every other embodiment discussed throughout the disclosure.

Figure 2:
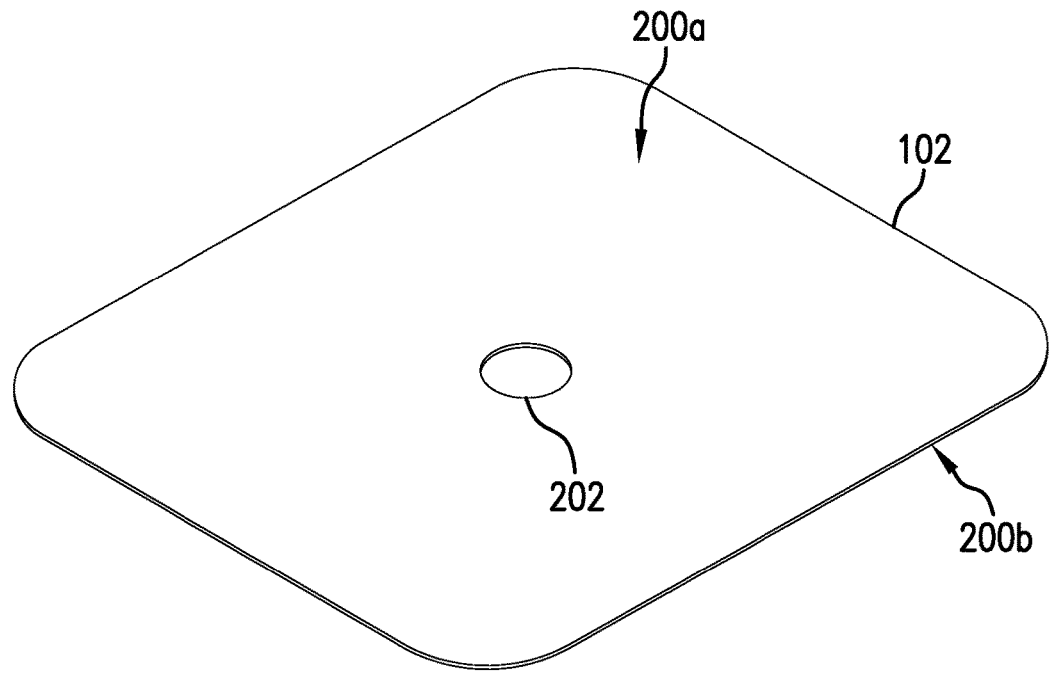
FIG. 2 is an isometric view of the patch.

FIG. 2 is an isometric view of the patch 102, in accordance with embodiments of the present invention. The patch 102 is defined by a top 200a and a bottom 200b. A thru-hole 202 traverses a thickness of the patch 102, the thickness being defined by the distance between the top 200a and the bottom 200b. The purpose of the thru-hole 202 is to provide access to an insertion surface of the subject. As illustrated, the thru-hole 202 is shown generally centered on the patch 102. However, in other embodiments the thru-hole 202 can be located anywhere on the patch 102, including, but not limited to along edges of the patch 102. In many embodiments the location of the thru-hole 202 is driven by balancing the size of the patch 202 and weight distribution of the on-body system 100.

In many embodiments, the patch 102 is defined by a plurality of different layers. For example, in one embodiment, the bottom 200b can be an adhesive cover or liner that protects an adhesive layer. Prior to placement of the on-body system 100 to a subject, the adhesive liner is removed thereby exposing the adhesive layer. The adhesive layer is intended to securely adhere the entirety of the on-body system 100 to insertion surface, typically a portion of the skin of the subject (not shown). The choice of adhesive can vary depending on the expected duration of the wear-period of the on-body system 100. Adjacent to the adhesive layer is another layer such as, but not limited to, a water vapor permeable layer with robust mechanical properties such as toughness, flexibility and resistance to, or ability to arrest tearing.

In some embodiments the patch 102 includes an additional layer of adhesive on the top 200a that secures the chassis 104 to the patch 102. Other embodiments of the patch 102 can include additional or fewer layers such as additional liner release layers, additional layers of adhesive, and other layers to improve or enhance mechanical performance of the patch 102. Additionally, while the thru-hole 202 is illustrated as being circular, the thru-hole 202 could take a different shape including, but not limited, to a slit. Furthermore, while described as a thru-hole, in some embodiments the thru-hole may not go through every layer of a multilayer material. For example, in one embodiments the patch includes a self-sealing layer that the thru-hole does not traverse. In this embodiment, the self-sealing layer is pierced during insertion of the sensor and acts as a barrier to prevent fluid from flowing into the thru-hole. In select embodiments, after the thru-hole 202 is made in the plurality of layers, the thru-hole 202 is filled with a material that acts as a septum. For example, the thru-hole 202 can be filled, or skinned with a thin layer of silicone that self-seals after allowing the sharp and the sensor to pass thru. The purpose of creating a septum across the thru-hole 202 is to minimize the likelihood of fluid ingress to the on-body system from the wound created by the sharp and the sensor. As will be discussed below, additional seals can be formed within the on-body system to further minimize the likelihood of fluid ingress. The particular features discussed above are intended to be exemplary and should not be construed as limiting.

Figure 3A:
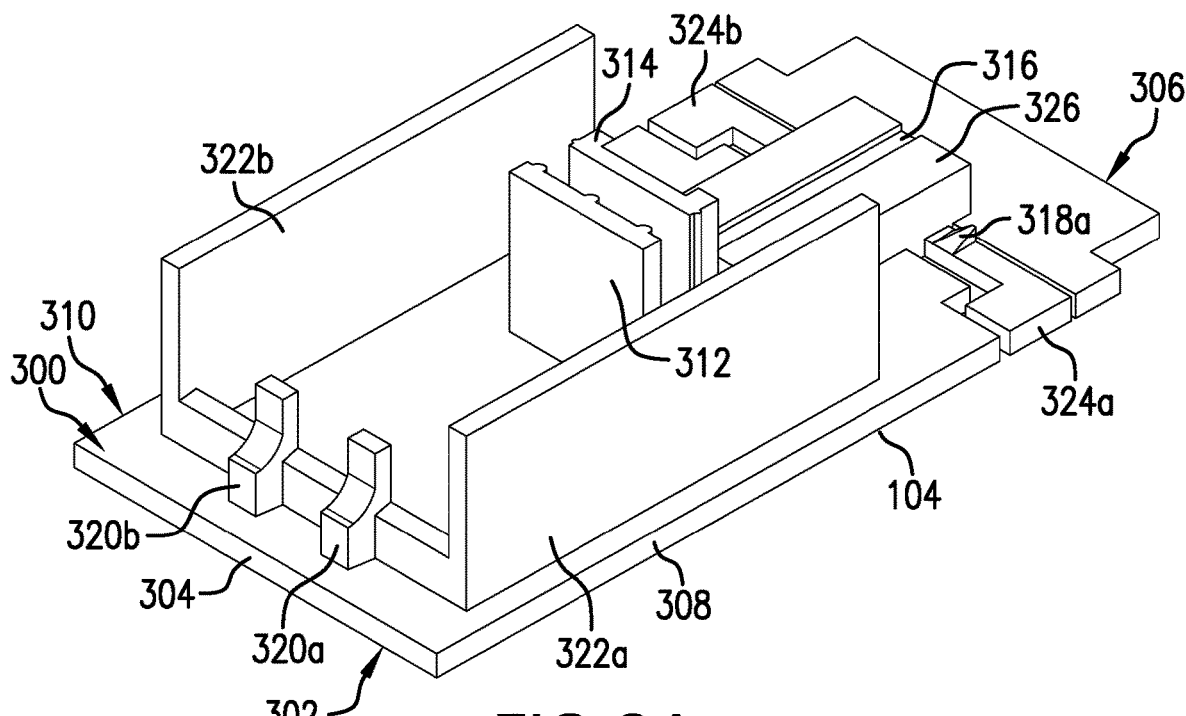
FIGS. 3A and 3B are different views of the chassis.
Figure 3B:
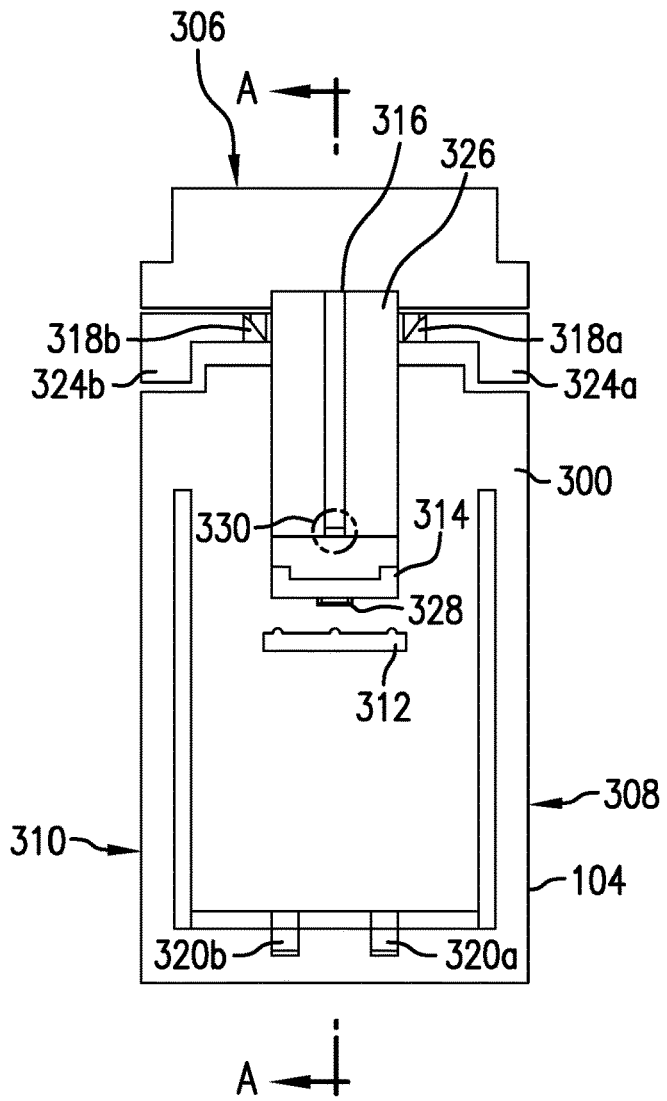

FIGS. 3A and 3B are different views of the chassis 104, in accordance with embodiments of the present invention. FIG. 3A is an isometric view while FIG. 3B is a top view of the chassis 104. Secured to the patch 102, the chassis 104 forms the foundation for the on-body system 100. In some embodiments adhesive applied to the bottom 302 of the chassis 104 secures the chassis 104 to the patch 102. In other embodiments, the chassis 104 is secured to the patch 102 via ultrasonic welding or an adhesive that is part of the patch 102. For general reference regarding feature locations, the chassis includes a top 300, a bottom 302, a front side 304, a back side 306, a right side 308 and a left side 310.

Toward the front side 304, the chassis 104 includes anchors 320a and 320b that enable coupling of energy storage 120 (FIG. 1) between the chassis 104 and the carriage 112 (FIG. 1). The anchors 320a and 320b are shown as two separate and distinct features but in other embodiments a single anchor is used while in still further embodiments three or more anchors are used. Similarly, while the anchors 320a and 320b are illustrated as posts, the configuration, which includes shape, placement and/or location, of the anchor or anchors can change depending on implementation of energy storage 120. Generically, the anchors 320a and 320b should be viewed as singular or plural attachments points that enable coupling between the chassis 104 and the carriage 112 via the energy storage 120.

The chassis 104 further includes sidewalls 322a and 322b that constrain displacement of the carriage 112 as it moves from back 306 toward the front 304. In some embodiments the sidewalls 322a and 322b are sized to reinforce structural rigidity of the cover 116. In other embodiments, materials savings and cost savings limit the height of the sidewalls 322a and 322b so they do not reinforce structural rigidity of the cover 116. Between the sidewalls 322a and 322b is a first guide 312 and a second guide 314 that are intended to constrain the sharp carrier 110 (FIG. 1) to a substantially vertical movement. Located between the first guide 312 and the second guide 314 is a sharp opening 328 that traverse through the entirety of the chassis from the top 300 to the bottom 302. The sharp opening 328 enables the sharp 108 (FIG. 1) to pass through the chassis 104 and achieve a sharp insertion depth below the insertion surface of the subject.

The chassis 104 further includes release features 324a and 324b along with carriage retainers 318a and 318b. Carriage retainers 318a and 318b are intended to prevent release of the carriage from a first position until actuation of release features 324a and 324b. As illustrated in FIGS. 3A and 3B, the carriage retainers 318a and 318b are features that engage with the carriage 112 in the first position and prevent the carriage 112 from moving to a second position. In many embodiments, once the carriage 112 has move to the second position, the carriage retainers 318a and 318b can be further utilized to secure the electronics module into the second position. Throughout this disclosure, the term "first position" should be construed as meaning the carriage 112 (FIG. 1) is positioned within the chassis ready to insert the sensor. Alternatively, the term first position can be construed to mean the energy storage is actively storing energy and is capable of delivering the stored energy to the carriage. Accordingly, in reference to the Figures, this would mean the carriage biased toward the back 306 of the chassis 104. Likewise, the term "second position" should be construed as meaning the carriage 112 (FIG. 1) is positioned within the chassis as if the sensor has already been inserted. Alternatively, the term second position can be construed to mean the energy storage is depleted and is no longer storing energy. Accordingly, in reference to the Figures, this means the carriage is biased toward the front 304 of the chassis 104.

Returning to FIGS. 3A and 3B, the release features 324a and 324b are flexible tabs that when depressed, disengage the carriage retainers 318a and 318b from the carriage 112 allowing the carriage 112 to traverse into a second position within the chassis 104. The illustrations and description regarding the release features 324a and 324b along with carriage retainers 318a and 318b are exemplary. Other embodiments can implement various combinations of singular or plural release features and/or carriage retainers. Furthermore, the location of the carriage retainer upon the release feature should not be construed as limiting. Rather, the carriage retainer or retainers along with release features may be located at various locations on the chassis 104 or even on other components within the on-body system 100. Generically, actuation of a release feature enables the carriage to be displaced from a first position to a second position.

From the second guide 314, moving toward the back 306 of the chassis 104 is a sensor block 326 that includes both a sensor channel 316 and a sensor aperture 330. The sensor channel 316 is a depression within the sensor block 326 that accommodates the sensor assembly 106 throughout an insertion process. Specifically, prior to, during and after insertion, a portion of the sensor assembly 106 is contained within the sensor channel 316. In many embodiments the sensor channel 316 is sized to be slightly wider than the sensor assembly 106. Additionally, in many embodiments, the sensor channel 316 is defined at a depth at least the thickness of the sensor assembly below a top surface of the sensor block 326. Accordingly, the sensor channel 316 can help guide the sensor assembly 106 during the insertion process.

The sensor aperture 330 is located at an end of the sensor channel 316 closest to the front 304. The sensor aperture 330 is an opening within the chassis 104 that allows the sensor assembly 106 to pass from the top 300 to the bottom 302 of the chassis 104 during the insertion process. In some embodiments, the sensor aperture 330 is an additional potential septum location that helps minimize the likelihood of moisture or liquid ingress near the electrical contacts.

Figure 3C:
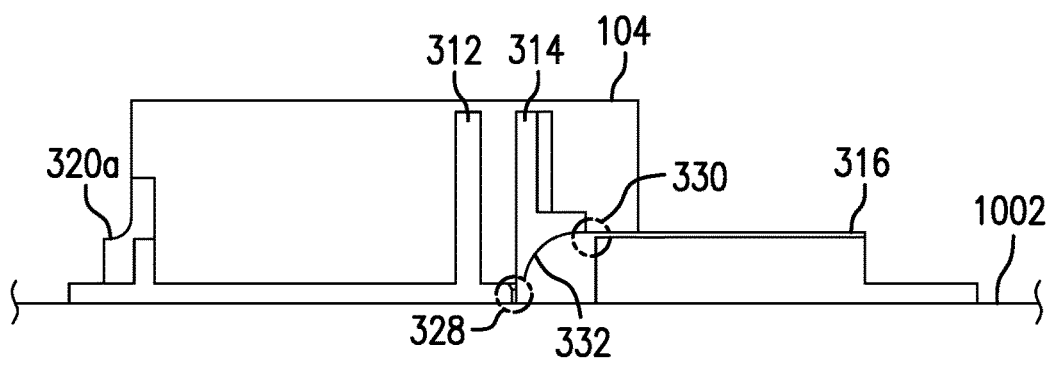
FIG. 3C is a cross-section view A-A of the chassis in FIG. 3B.

FIG. 3C is a cross-section view A-A of the chassis 104 in FIG. 3B, in accordance with embodiments of the present invention. FIG. 3C illustrates that the sensor aperture 330 opens to a void that includes a sensor deflector 332 on the bottom 302 of the chassis 104. Alternate embodiments partially or completely fill the void to provide additional guidance to deflect the sensor from substantially horizontal to vertical displacement. Similarly, the sharp opening 328 can be seen passing through the chassis 104 between the first guide 312 and the second guide 314. The purpose of the sensor deflector 332 is to deflect the sensor assembly 106 from a substantially horizontal position to a substantially vertical position. In FIG. 3C the sensor deflector 332 aligns with the sensor aperture 330 at a substantially 90 degree angle to the insertion surface. However, various other embodiments include a sensor deflector and first and second guides that enable insertion at angles other than substantially 90 degrees to the insertion surface 1002.

A coincidence between the sharp opening 328 and the sensor deflector 332 enables the sensor to be cooperatively inserted with the sharp 108. Cooperative insertion is intended to describe an insertion process where the sensor assembly 106 is participating in displacing tissue rather than simply riding within a needle or cannula. Specifically, with cooperative insertion the need for a needle that encapsulates or partially surrounds the sensor assembly is obviated because the mechanical properties of the sensor assembly 106 enable the sensor assembly 106 to create it's own wound channel to the desired insertion depth beneath the insertion surface. With cooperative insertion, the intended purpose of the sharp is to penetrate the more resilient outer layers of the skin and allows the mechanical properties of the sensor assembly to drive the sensor to the desired insertion depth.

Note that sensors disposed on rigid or brittle materials may not be ideal for use within the on-body system 100 because of their inability to navigate the sensor deflector 332 without fracturing or compromising their mechanical integrity. As previously discussed, sensors using features and substrates described in U.S. patent application Ser. Nos. 15/472,194 and 15/455,155 are ideally suited for use within the on-body system 100 because the stainless steel substrate is robust and flexible enough to traverse the sensor deflector 332 without compromising the mechanical integrity of the sensor assembly. An additional benefit of using sensor assemblies based on stainless steel substrates is the ability to shape the distal end of the sensor assembly to further cooperative insertion via the sharp. Alternative embodiments utilize sensors based on different albeit flexible technologies such as, but not limited to optical fibers and the like. In still other embodiments, the sensor can be replaced or optionally supplemented with a flexible drug delivery catheter. Embodiments implementing a catheter may or may not require an introducer to keep the catheter pathway open during the insertion process. With embodiments utilizing a catheter, other components within the on-body system may require modification to accommodate the fluid path that is either self contained within the on-body system or requires a fluid communication connection to an infusion pump.

Figure 4A:
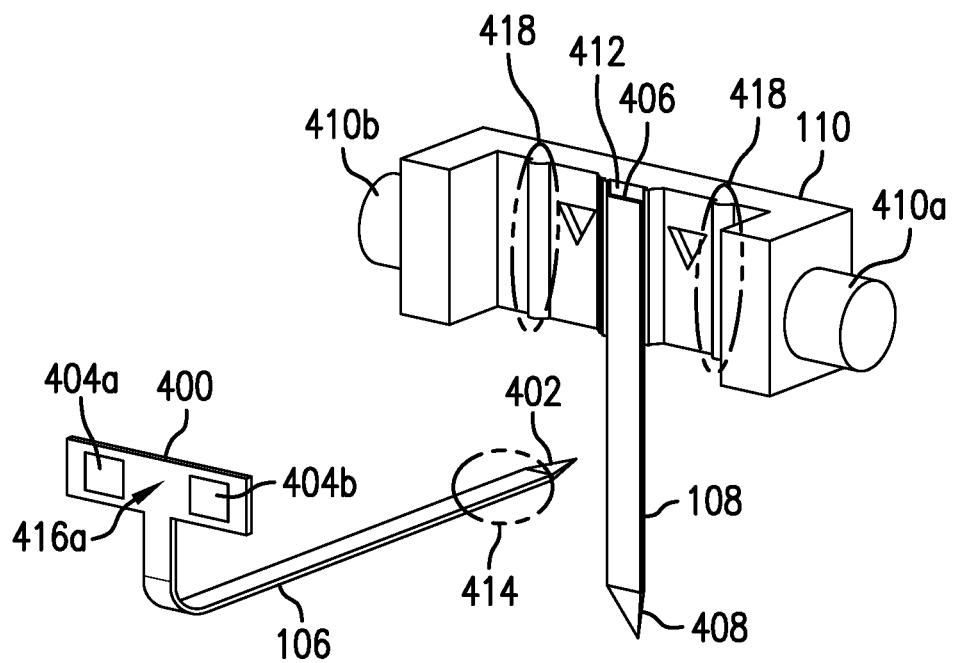
FIGS. 4A and 4B are exemplary isometric illustrations of components that are inserted into a subject.
Figure 4B:
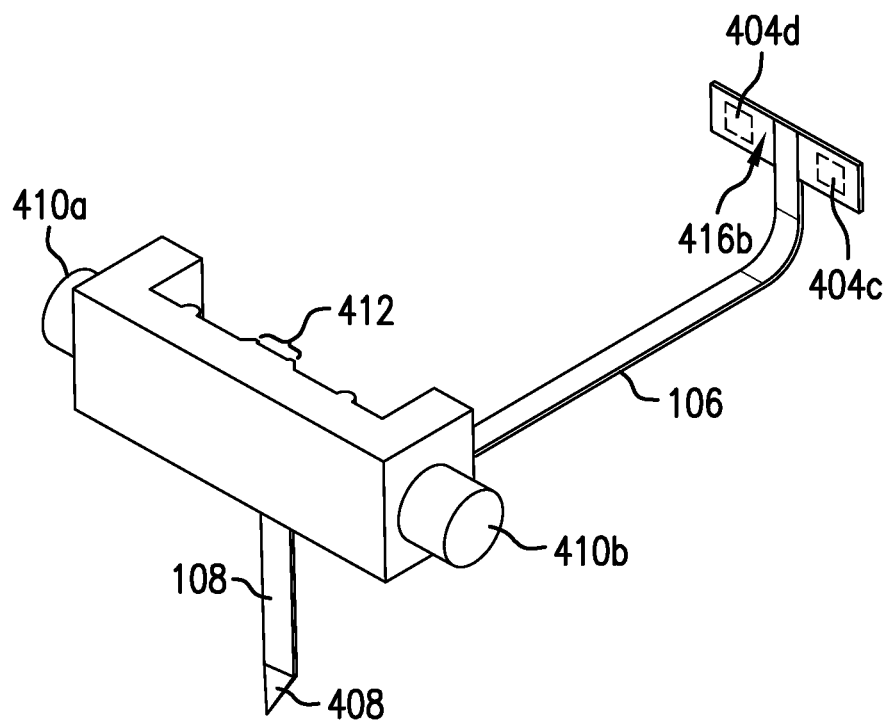

FIGS. 4A and 4B are exemplary isometric illustrations of components that are inserted into a subject, in accordance with embodiments of the present invention. FIGS. 4A and 4B each include the sensor assembly 106 along with the sharp carrier 110 and the sharp 108. The sensor assembly 106 has a proximal end 400 that further includes contact pads 404a and 404b. A distal end 402 of the sensor assembly 106 includes an approximate sensing area 414. The sensing area 414 is intended to include all surfaces and edges of the sensor assembly because various embodiments of sensor elements may be used within the sensor assembly 106. Additionally, the position and location of the contact pads with respect to the electrodes may be determined though folding or other manipulation of the proximal end of the sensor to separate the contact pads. Furthermore, additional contact pads can supplement contact pads 404a and 404b if necessary on face 416a. Alternatively, even more contact pads such as 404c and 404d can be formed on face 416b if necessary for proper operation of the sensor assembly 106. The illustration of the sensor assembly 106 shown in FIGS. 4A and 4B should not be construed as limiting. In other embodiments different sensor configurations, such as, but not limited to those described in U.S. patent application Ser. No. 15/455,155, which is herein incorporated by reference, can be used as part of the on-body system 100.

In preferred embodiments the sharp 108 has its sharp proximal end 406 fastened to the sharp carrier 110. The technique to fasten the sharp proximal end 406 to the sharp carrier 110 includes mechanical bonding such as, but not limited to adhesives, heat staking, ultrasonic welding, overmolding, or even mechanical fasteners such as screws, rivets and the like. The sharp carrier 110 further includes carrier pins 410a and 410b. The carrier pins 410a and 410b are intended to fit within cam profiles within the carriage 112. Furthermore, the sharp carrier 110 is defined to fit between the first guide 312 and the second guide 314 of the chassis 104. Friction reducer 418 is visible on the sharp carrier 110. The inclusion of friction reducer 418 is to reduce both static and dynamic friction between the sharp carrier 110 and the first guide 312 and the second guide 314. While specifically described in reference to the sharp carrier 110, friction reducer features can be implemented on other components within the on-body system, particularly, those moving relative to one another. The first and second guides 312 and 314 of the chassis restricting movement of the sharp carrier 110, and the attached sharp 108 to a substantially vertical displacement in accordance with the cam profiles within the carriage.

Note that both the distal end 402 of the sensor assembly 106 and the sharp distal end 408 can be shaped to improve piercing capability. In many embodiments, the sharp distal end 408 is formed like the tip of a #2 X-acto blade or #11 X-acto blade or scalpel, where the tip is not down a centerline, but rather on one side of the centerline. In other embodiments the sharp distal end 408 remains flat but is formed like a broadhead arrow, where the tip is located along the centerline of the sharp. Various embodiments utilize different sharp termination of the distal end 402 and the sharp distal end 408. Generically, it may be preferred to have at least one or both of the distal end 402 or the sharp distal end 408 formed to a piercing point to aid in insertion. If only one of the distal end 402 and the sharp distal end 408 are formed to a piercing point, it may be preferable to form the piercing point on the whichever element contacts the insertion surface first. In embodiments where the distal end 402 and the sharp distal end 408 concurrently contact the insertion surface, either may be formed into the piercing point.

Figure 5A:
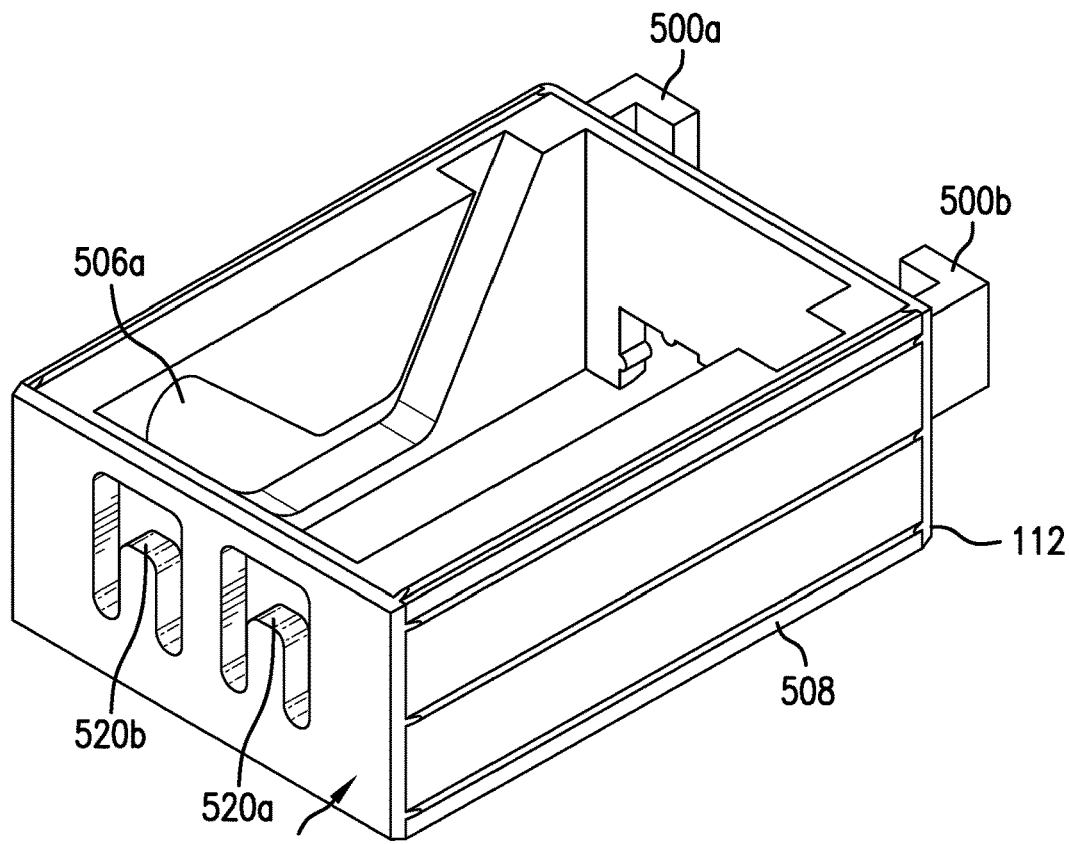
FIGS. 5A and 5B are isometric views of the carriage.
Figure 5B:
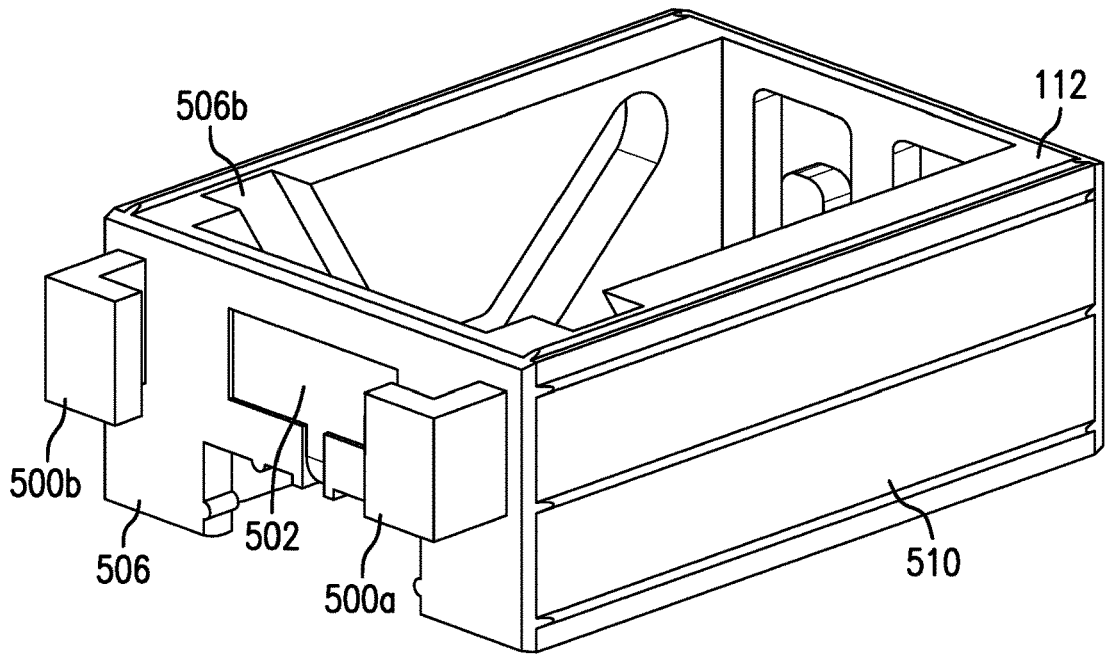

FIGS. 5A and 5B are isometric views of the carriage 112 in accordance with embodiments of the present invention. The carriage 112 is intended to move within the chassis 104 and impart substantially horizontal movement to the sensor assembly 106 while also imparting vertical movement to the sharp carrier and associated sharp. Horizontal movement of the carriage 112 is imparted via attachment points 520a/520b and previously discussed energy storage 120 (FIG. 1). In various embodiment energy storage 120 is a single rubber band or multiple rubber bands that are secured to attachment points 520a/520b of the carriage 112 and the anchors 320a/320b of the chassis 104 (FIGS. 3A and 3B). The illustration of the attachment points 520a/520b is intended to be exemplary and should not be construed as limiting. Attachment points 520a/520b can be various shapes in order to accommodate a variety of energy storage systems. Furthermore, in additional embodiments, additional or fewer attachment points can be utilized, again, depending on the type of energy storage system or if multiple types of energy storage systems are being utilized.

Vertical movement of the sharp 108 and sharp carrier 110 is achieved while the carriage 112 is moving horizontally via cam paths 506a and 506b. Carrier pins 410a/410b (FIGS. 4A/4B) fit into cam paths 506a/506b. First guide 312 (FIGS. 3A, 3B, 3C) and second guide 314 (FIGS. 3A, 3B, 3C) prevent the sharp carrier 110 from translating horizontally enabling the cam paths 506a/506b to impart vertical movement of both the sharp and sharp carrier.

On carriage back 506 retainers 500a/500b couple the electronics module 114 to the carriage. Like the attachment points 520a/520b, the retainers 500a/500b shown in the Figures are intended to be illustrative rather than limiting. Similarly, fewer or more retainers 500a/500b can be utilized in various embodiments depending on the coupling scheme between the carriage 112 and electronics module 114.

A connector block 502 is also located on the carriage back 506. The connector block 502 is intended to locate and retain the proximal end 400 (FIGS. 4A/4B) of the sensor assembly 106. The proximal end 400 (FIGS. 4A/4B) of the sensor assembly 106 can be secured or affixed to the connector block 502 portion of the carriage 112 using a variety of techniques such as, but not limited to bonding, adhering, heat staking, overmolding, and the like. The sensor assembly 106, having the proximal end 400 affixed to the connector block 502, is then free to rest in the sensor channel 316 (FIGS. 3A, 3B, 3C).

Figure 6A:
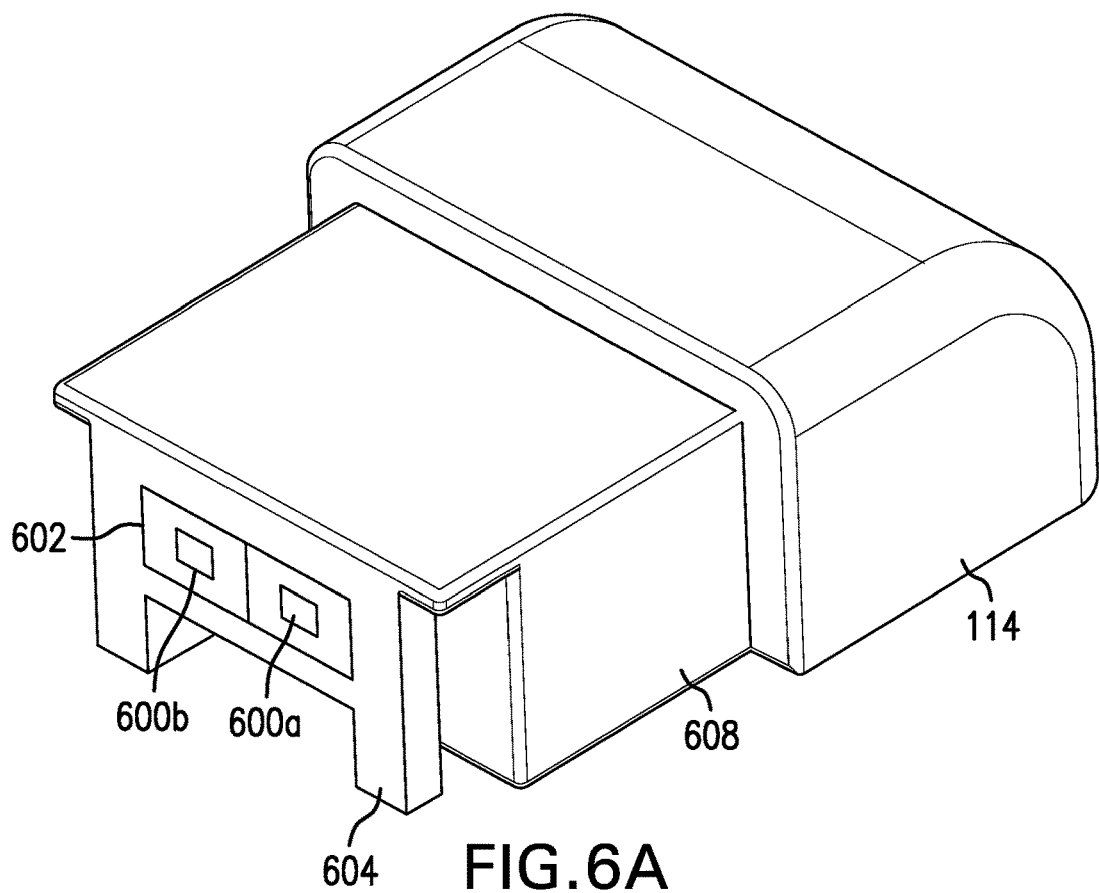
FIG. 6A ad 6B are various illustrations of the electronics module.
Figure 6B:
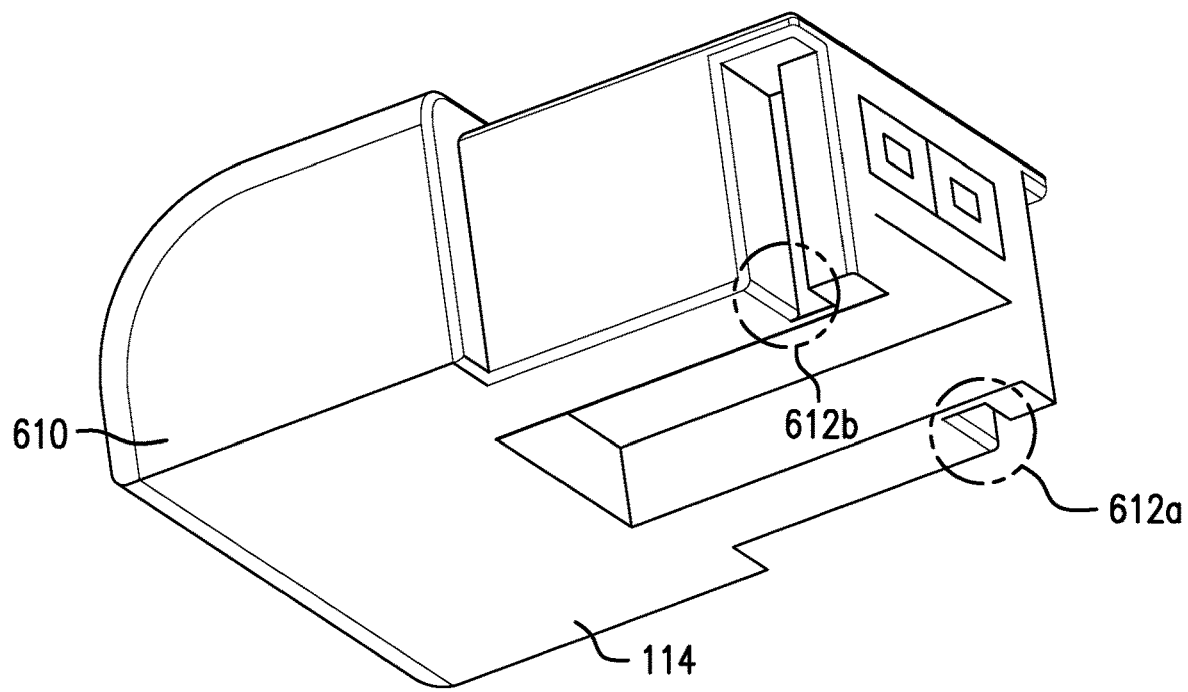

FIGS. 6A and 6B are various illustrations of the electronics module 114, in accordance with embodiments of the present invention. The electronics module 114 is intended to house electronic components of the on-body system 100. Accordingly, the electronics module 114 may contain a circuit board that electronically connects components such as, but not limited to a power supply, a potentiostat, communications and computing hardware along with memory that stores instructions for the computing hardware and data acquired from the sensor assembly 106. In preferred embodiments, the communications hardware includes radios capable of secure or encrypted two-way communication such as commercially available systems utilizing standardized protocols like Bluetooth SMART, ZigBee, ANT by Dynastream, WiFi, and the like. In other embodiments, proprietary secure wireless standards or systems or even wired connections may be implemented within the electronics module 114. An exemplary embodiment of a wired connection includes, is not limited to connections such as micro-USB, mini-USB or the suite of USB type-C connectors.

Mechanically, the electronics module 114 includes retention features 612a/612b located toward electrical module front 604. The retention features 612a/612b are intended to interface with retainers 500a/500b on the carriage 112 and secure the electronics module 114 to the carriage 112. Securing the electronics module 114 to the carriage 112 enables electrical contact to be made between the sensor assembly 106 secured to the carriage 112 and the electronics module 114.

In many embodiments, electrical mates 600a/600b are found on electronic module front 604. Electrical mates 600a/600b are positioned to make electrical contact with contact pads 404a/404b (FIG. 4A) when the sensor assembly is mounted in the carriage 112. In some embodiments, the electrical mates 600a/600b are spring features anchored to a circuit board within the electronics module 114. In other embodiments, the electrical mates 600a/600b are electrical contact pads that are intended to interface with the sensor assembly. To improve the water resistance of the on-body system, gasket 602 can be applied around the electrical mates 600a/600b.

Some embodiments of the electronics module 114 are intended to be reusable (durable) while other embodiments are intended to be only used once before being discarded (disposable). One difference between durable and disposable electronics modules is the implementation of the power supply. With durable embodiments, it can be advantageous to include a rechargeable power supply, such as, but not limited to rechargeable batteries or capacitors. The requisite hardware required to recharge the batteries or capacitors would also be required such as, but not limited to inductive charging hardware, a charging port, and/or the incorporation of solar cells. Alternatively, disposable embodiments can implement single use batteries. Another potential difference between durable and disposable embodiments is the selection of materials. As durable embodiments may be required to undergo periodic or at least multiple cleanings, a more durable/cleanable material may be selected.

Figure 7A:
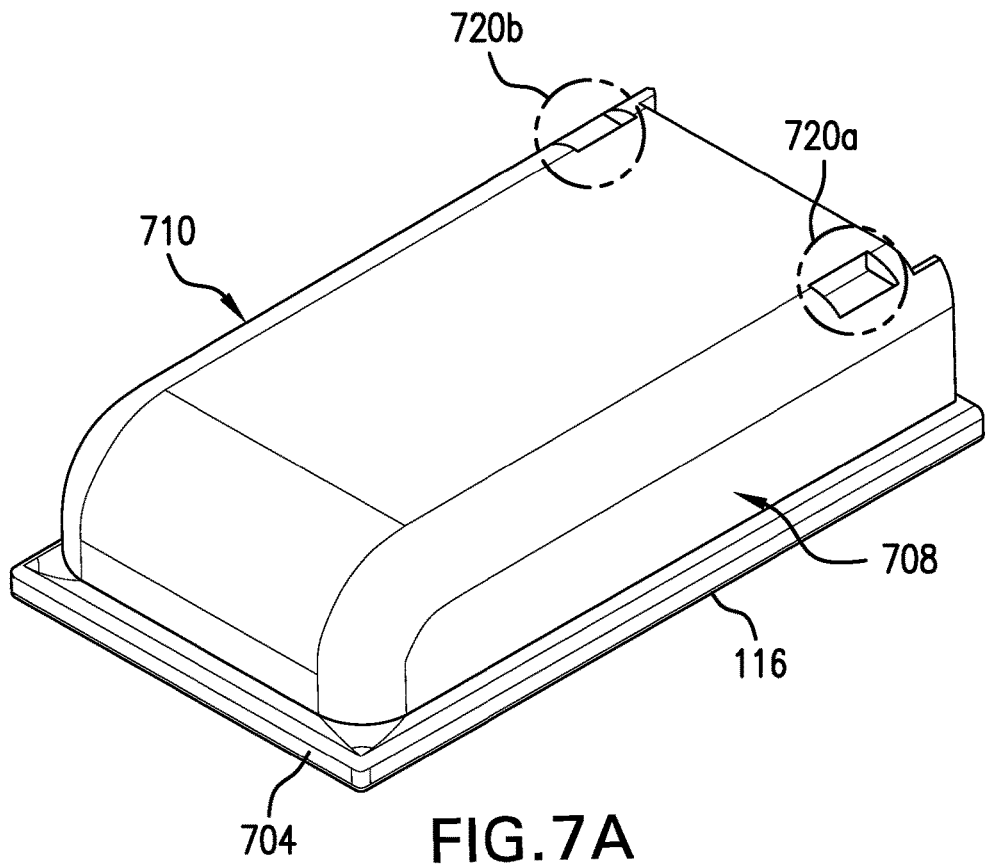
FIG. 7A is an isometric view of the cover.
Figure 7B:
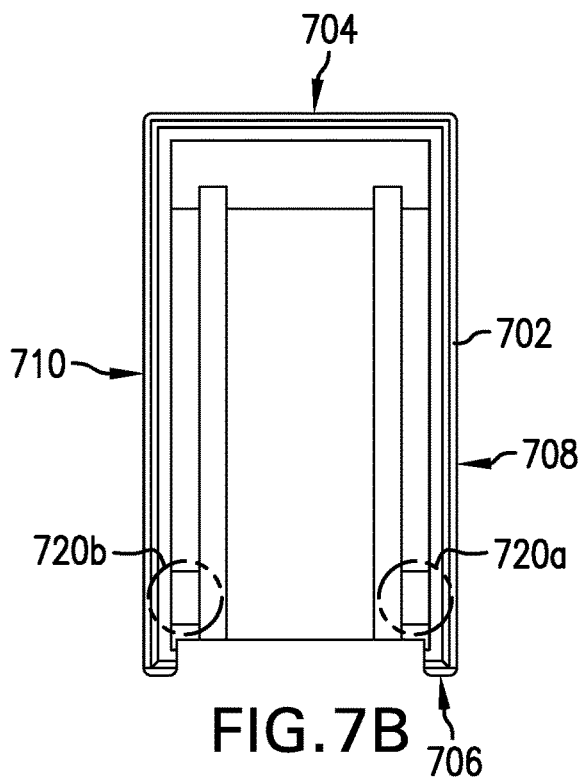
FIG. 7B is a bottom view of the cover.

FIG. 7A is an isometric view of the cover 116 while FIG. 7B is a bottom view of the cover 116, in accordance with embodiments of the present invention. The cover 116 is intended to provide mechanical protection to the components within the on-body system 100. As many embodiments of the on-body system 100 are intended to be used in an ambulatory environment the cover 116 is preferably made from durable, tough, robust non-leaching, non-toxic material such as, but not limited to TRITAN or POLYCARBONATE. The cover 116 has a cover front 704, cover right 708, cover left 710 and cover back 706. Additionally, in some embodiments the cover 116 further includes cover receivers 720a and 720b. The cover receivers 720a/720b are intended to allow the actuator 118 (FIG. 1) to actuate the release features on the chassis. Embodiments using alternative actuator designs may alter the inclusion and/or location of the cover receivers 720a/720b. The cover 716 can be an integral component in establishing or enhancing the resistance of moisture ingress. In many embodiments, along the cover bottom 702 a gasket material can be overmolded onto the cover 116 itself, thereby making the gasket an integrated component of the cover 116. To improve the performance of the integrated gasket, the chassis can include a mating feature such as a rib or depression that is intended to enhance the performance of the gasket integrated into the cover 116. Seals and gaskets are implemented throughout the design of the on-body system 100 to ensure it is capable of receiving an International Protection Marking of at least IPX7.

Figure 8:
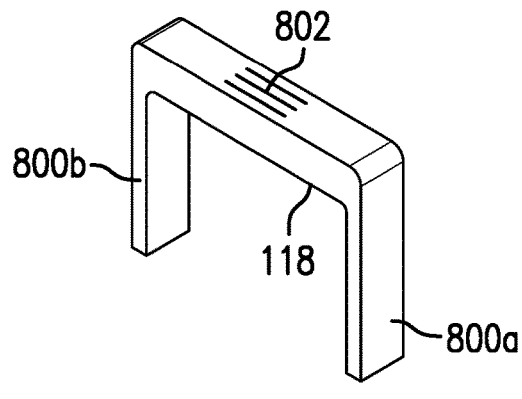
FIG. 8 is an isometric view of the actuator.

FIG. 8 is an isometric view of the actuator 118, in accordance with embodiments of the present invention. The actuator 118 interfaces with the release features 324a/324b (FIGS. 3A/3B) of the chassis 104 (FIGS. 3A/3B). In the exemplary embodiment illustrated in FIG. 8, specifically right arm 800a and left arm 800b interface with release feature 324a and release feature 324b, respectively. In many embodiments, the actuator 118 includes optional features such as a traction area 802. The traction area 802 can include one or more raised or lower surfaces that improve purchase of a digit upon the actuator 118.

The embodiment shown in FIG. 8 is intended to be exemplary and should not be construed to limit further embodiments of actuator mechanisms. Furthermore, while the actuator 118 in FIG. 8 is a single discrete piece, other embodiments of actuators can be integrated with previously discussed components or even be multipiece mechanisms that require single or multiple manipulations of interlocks and other mechanical interactions. Generically speaking, the actuator 118 interacts with other components of the on-body system to actuate movement of the carriage from the first position to the second position via the energy storage 120 regardless of how many actual parts or pieces are required to release the stored energy.

Figure 9:
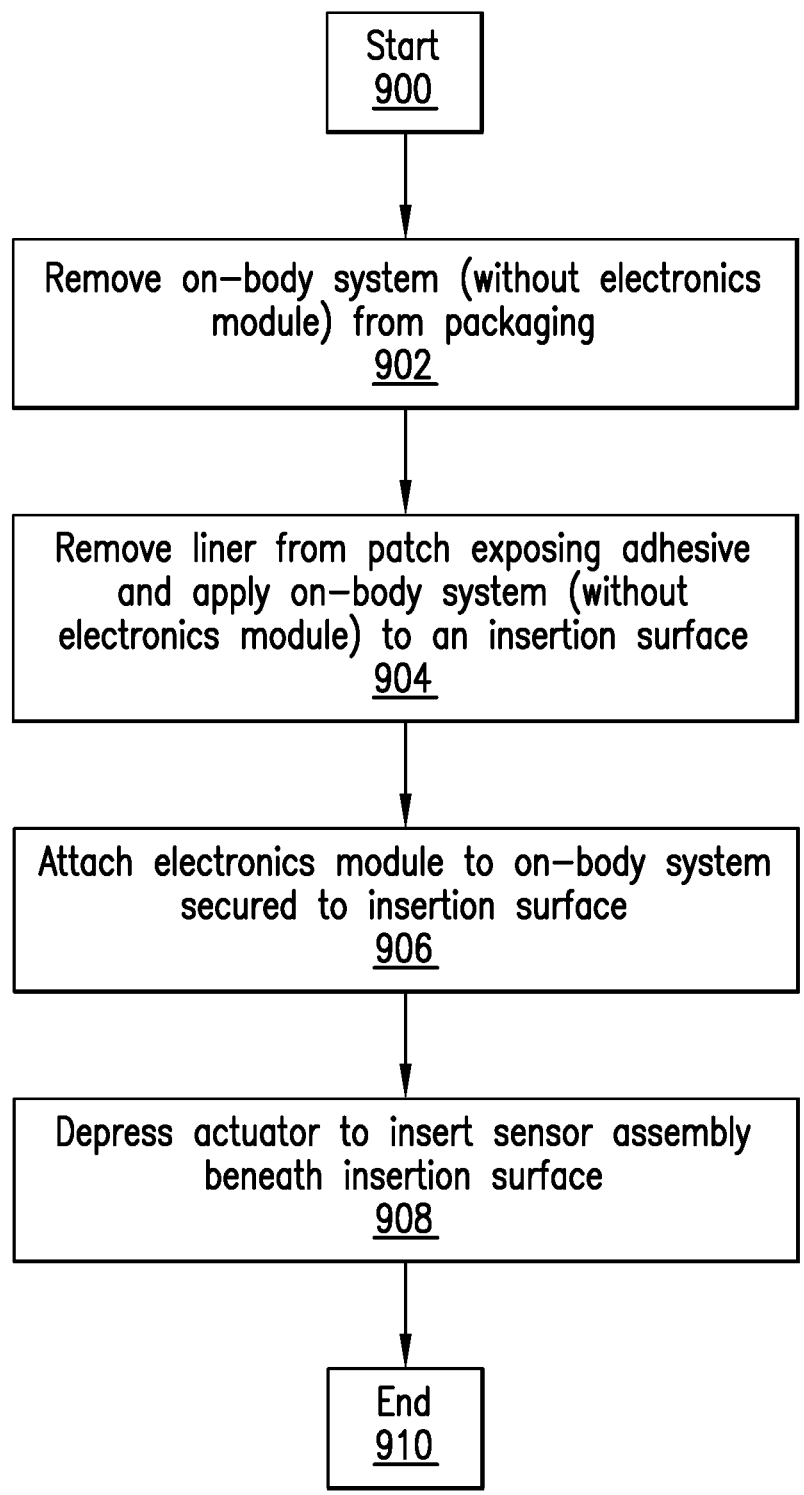
FIG. 9 is a flowchart describing exemplary operations to use the on-body system to insert a sensor below an insertion surface.

FIG. 9 is a flowchart describing exemplary operations to use the on-body system to insert a sensor below an insertion surface, in accordance with embodiments of the present invention. The operations shown in FIG. 9 encompass macro operations. As will be described below, each macro operation can encompass sub-operations, some of which are optional and intended to improve safe handling and operation of the on-body system.

The flowchart begins with start operation 900. Execution of operation 902 removes the on-body system 100 (without the electronics module 114) from packaging materials. In other embodiments, the electronics module 114 is initially disconnected from the remainder of the on-body system within the packaging materials but the act of removing the remainder of the on-body system from the packaging automatically couples the electronics module with the remainder of the on-body system. In still other embodiments, the electronics module is pre-connected to the remainder of the on-body system with an additional removable dielectric liner between the contact pads of the sensor assembly and the mating connector of the electronics module. The removeable dielectric liner being either manually or automatically removed prior to insertion of the sensor beneath the insertion surface.

Returning to FIG. 9, with operation 904 a protective liner layer is removed from the bottom of the patch exposing adhesive and the on-body system (without the electronics module) is applied to the insertion surface. In some embodiments, removal of the on-body system from the packaging automatically removes the protective liner layer. In these embodiments, operation completion of operation 902 is followed by operation 906. Operation 906 results in the coupling of the electronics module 114 to the on-body system that has already been adhered to the insertion surface. Note that in other embodiments, sub-operations from operations 906 and 904 can be interchanged resulting in the electronics module being attached to the on-body system prior to removal of the liner layer or after the removal of the liner layer but prior to application of the on-body system to the insertion surface.

Regardless of the order of operations 904 and 906, connection of the electronics module to the on-body system results in electrical contact being made between the contact pads 404a/404b of the sensor assembly and the electrical mates 600a/600b of the electronics module. This enables power to be delivered to the sensor assembly prior to inserting the sensor below the insertion surface. Additionally, electrically connecting the sensor and electronics module allows components within the electronics module, such as clocks, processors, communications modules and the like, to begin operating. One benefit of powering the sensor assembly and electronics module before insertion is the ability to run diagnostic tests on the sensor and/or the electronics module. If the sensor and electronics module pass the diagnostic test audible, visual or tactile feedback can be provided to the user via the electronics module or an associated application that is paired with the electronics module.

An additional benefit of electrifying the sensor before insertion is the opportunity to measure insertion success via electrical measurements. In some embodiments, if measured values indicate that insertion was less than ideal, secondary energy storage mechanisms or translation mechanisms can be actuated to attempt to improve the insertion depth of the sensor. For example, after the carriage has translated into the second position, measurements from the sensor indicate that insertion could be improved by attempting to insert the sensor further into the subject. In particular embodiments, the cam path can include some additional run out that can insert the sensor to a greater depth via an electric motor powered within the electronics module.

With operation 908 the actuator releases the carriage from the first position. Assisted by energy storage, the carriage and coupled electronics module transition from the first position to the second position by traversing laterally across the chassis. Throughout the transition from first position to second position, the proximal end of the sensor assembly is secured to the connector block of the carriage resulting in the proximal end of the sensor traversing substantially parallel to the insertion surface throughout the insertion process. While the proximal end of the sensor assembly is restricted to traversing substantially parallel to the insertion surface, the distal end of the sensor assembly is inserted below the insertion surface.

Because the sensor assembly is intentionally deformed during the transition from the first position to the second position, the sensor assembly must have robust mechanical properties. For example, both the substrate and electrode layers disposed on the substrate must be able to survive the intentional deformation during insertion. Prior to being placed below the insertion surface the sensor assembly must navigate the sensor deflector 332 (FIG. 3C). In the first position, many embodiments have the distal end of the sensor assembly on the sensor channel 316 (FIG. 3C), not within the sensor aperture 330 (FIG. 3C). In other embodiments, the distal end of the sensor assembly is placed just within the sensor aperture. During the transition between the first position and the second position, the sensor deflector redirects the lateral/horizontal movement of the carriage relative to the chassis into vertical displacement toward and below the insertion surface. Consequently, the sensor assembly must have mechanical properties that allow it to survive substantial flexing without breaking.

In many embodiments, the distal end of the sensor is cooperatively inserted below the insertion surface with the aid of the sharp. As cooperative insertion implies, the sensor cooperatively works with the sharp to create the wound channel and extraction of the sharp leaves the sensor within the wound channel. The sharp contemplated in preferred embodiments is a thin solid with a pointed end, the end further being sharpened. One advantage of using a sharp is the significantly lower cost than a similar needle. In many embodiments, the sharp is intended to pierce the insertion surface, typically bare skin, creating a narrow slit for the sensor assembly to enter. After the sharp creates a slit in the tougher, more resilient skin, the sensor assembly is inserted below the insertion surface. The mechanical properties of the sensor assembly are robust enough to continue insertion further below the insertion surface with or without continued assistance from the sharp. Because the sensor can create its own wound channel, cooperative insertion reduces localized trauma compared to insertion performed with a needle that must accommodate a sensor. With cooperative insertion the insertion depth of the sharp beneath the insertion surface can be minimized. An alternate perspective would be that the mechanical properties of the sensor assembly allow the sensor assembly to be inserted further below the insertion surface that the insertion depth of the sharp.

Cooperative insertion as discussed above is distinguishable from insertion that utilizes a needle. First and foremost, needles typically used to insert sensors, are commonly hollow or at least partially hollow. In many embodiments where needles are used for insertion, the sensor is placed either within the hollow of the needle or within a cannula associated with the needle. Accordingly, with needle based insertion, the needle creates the wound channel and the sensor is left behind within the wound channel. Cooperative insertion is different than needle based insertion in that once through the skin, the sensor assembly itself, rather than a needle, is capable of creating the wound channel. In some embodiments, cooperation between a sharp and the sensor is not required as the sensor has robust qualities that enable the sensor itself to achieve piercing the skin and creating the wound channel to the desired insertion depth.

During operation 908 additional sub-operations includes retraction of the sharp and optional storage of the sharp. After piercing the skin to enable cooperative insertion, the sharp is retracted to a position above the insertion surface via the cam profile within the carriage. In some embodiments, the second position coincides with the cam profile locking the sharp into a storage position that is fixed. The storage position is intended to ensure the carriage does not translate backwards enabling the sharp to be lowered below the insertion surface. After the carriage has reached the second position, insertion is complete with end operation 910. After insertion is complete, the entirety of the on-body system remains in place for the duration of the sensor lifespan, or an intended wear-period. With the on-body system described herein, there is no separate insertion tool that must be disposed of or reused. Similarly, there is no separate sharp or needle that must be disposed of after insertion of the sensor assembly. In many embodiments, after the sensor lifespan has been exhausted, the entire on-body system is removed and properly disposed of. In other embodiments, the electronics module can be optionally reused. Alternatively, in lieu of utilizing a sharp that requires disposal or sharp safe storage after insertion, some embodiments do not include a sharp and insertion is accomplished relying on the mechanical properties of the sensor assembly. These embodiments may include additional support for the sensor assembly as it navigates the sensor deflector. Specifically, the sensor deflector may be configured to support the sensor assembly from the bottom resulting in the sensor assembly emerging from a slit in the carriage.

A common sub-operation that can be performed with each operation is the release of interlocks. Interlocks can be implemented within the on-body system to reduce the likelihood of unintentional actuation. For example, in many embodiments a sub-operation of operation 902 is the release of an interlock when the on-body system is removed from the packaging. This can be something as simple as releasing a pogo spring or engaging or disengaging magnetic interlocks. Similarly, additional interlocks can be engaged/disengaged when the on-body system is applied to the insertion surface. A sub-operation of operation 906 is releasing an interlock that prevents activation of the actuator only when the electronics module has been attached to the chassis. The particular operations and sub-operations described above are considered exemplary and should not be construed as limiting. Additional or fewer operations can be executed and still fall within the scope of this disclosure.

Figure 10A:
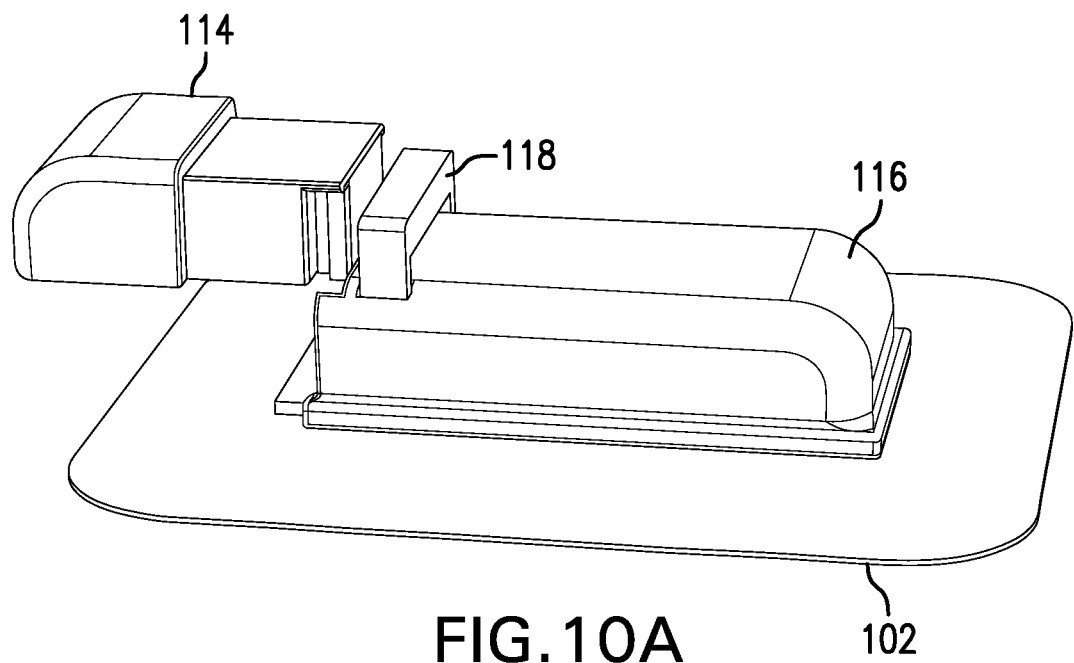
FIGS. 10A and 10B are an pseudo-isometric and cross-sectional views of the on-body system in a first position prior to the electronics module being attached.
Figure 10B:
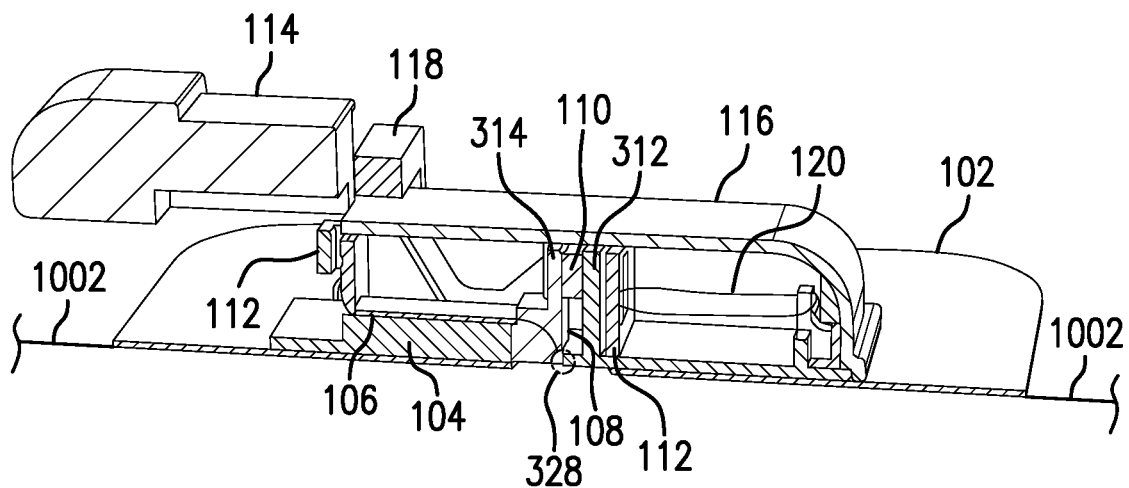

FIGS. 10A and 10B are an pseudo-isometric and cross-sectional views of the on-body system in a first position prior to the electronics module being attached, in accordance with embodiments of the present invention. With regard to the flowchart in FIG. 9, what is shown in FIGS. 10A/10B would be prior to executing operation 906. Accordingly, the retention feature 612b (FIG. 6B) is shown prior to engaging with retainer 500a (obstructed by the cover, but found in FIG. 5B). The cross-section illustrated in FIG. 9B further shows individual components within the on-body system prior to execution of operation 906 (FIG. 9). For simplicity, the interior of the electronics module 114 has been rendered as solid whereas actual embodiments would contain the previously discussed electronic components and mechanical hardware. In FIGS. 10A and 10B the carriage 112 is shown in the first position resulting in the energy storage 120 being loaded and upon actuation, the carriage 112 will transition from the first position to the second position. For illustrative simplicity, throughout this disclosure the energy storage 120 has been illustrated as a rubber band. Other embodiments utilize different energy storage systems such as, but not limited to springs, pressurized pistons, electrical batteries and motors, smokeless powder or explosive charges. As shown in FIG. 10B, the sharp carrier 110 is between the first guide 312 and the second guide 314 while the sharp 108 has not entered the sharp opening 328. Also shown in FIG. 10B is the sensor assembly 106 within the sensor channel 316.

Figure 11A:
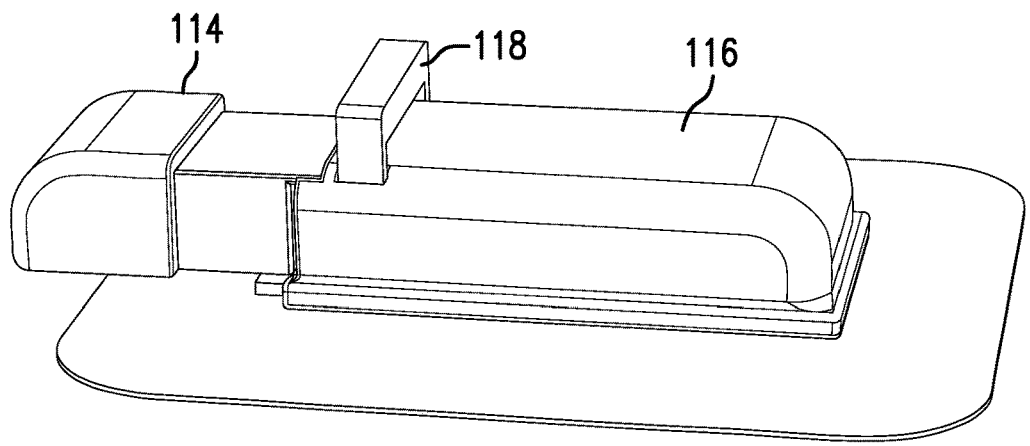
FIGS. 11A and 11B are a pseudo-isometric and a cross-sectional view of the on-body system in a first position after the electronics module has been attached.
Figure 11B:
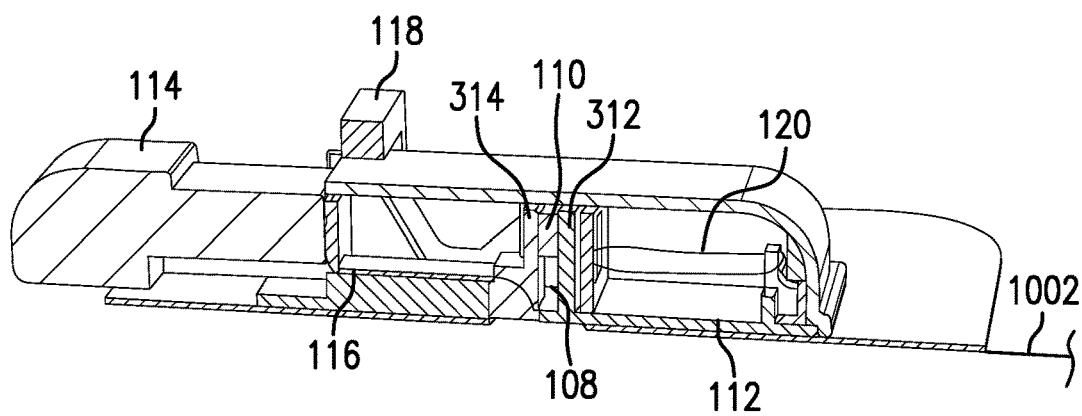

FIGS. 11A and 11B are a pseudo-isometric and a cross-sectional view of the on-body system in a first position after the electronics module has been attached, in accordance with embodiments of the present invention. With reference to FIG. 9, the exemplary illustrations in FIGS. 11A/11B coincide with completion of operation 906. The difference between FIGS. 11A/11B and 10A/10B is that the electronics module 114 has been fully coupled or engaged with the carriage 112. While not visible in the FIGS. 11A/11B, electrical connectivity has been established between the electrical mates 600a/600b of the electronics module and the contact pads 404a/404b of the sensor assembly.

Electrically connecting the sensor assembly and electronics module enables power delivery to the sensor prior to beginning the insertion process. This can be beneficial because it can reduce run-in time for the sensor along with allowing a diagnostic check of the sensor assembly and the electronics module before proceeding with insertion. In various embodiments, different permutations of powering the sensor and performing diagnostic tests of either the sensor assembly, the electronics module or both the sensor assembly and electronics module are performed.

Furthermore, in still other embodiments, upon coupling the electronics module with the carriage and associated sensor assembly, rather than powering up all of the electronics module, discrete components or individual systems within the electronics module can be powered up. For example, the potentiostat and/or the communication system can be powered up. Powering the communication systems within the electronics module can allow pairing between a controller or display. The benefits of pairing prior to insertion is optionally displaying instructions or even instructive videos to the user via an integrated application.

Figure 12A:
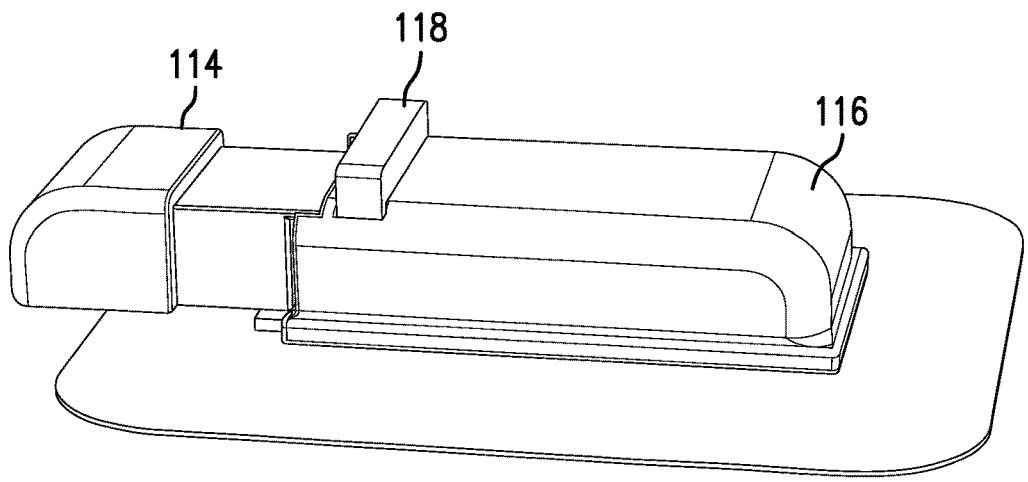
FIGS. 12A and 12B are a pseudo-isometric view and a cross-sectional view of the on-body system transitioning between a first position and a second position.
Figure 12B:
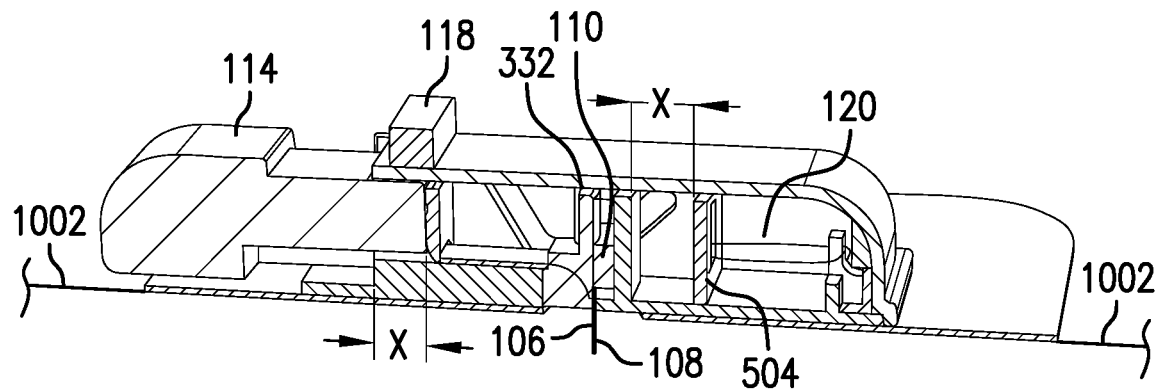

FIGS. 12A and 12B are a pseudo-isometric view and a cross-sectional view of the on-body system transitioning between a first position and a second position, in accordance with embodiments of the present invention. With reference to FIG. 9, the exemplary illustrations in FIGS. 12A/12B coincide with just after execution of operation 908 where the carriage is transitioning between the first and second positions. Comparing FIG. 11B and FIG. 12B, the actuator 118 has been depressed resulting in the energy storage 120 moving the carriage 112 and electronics module 114 parallel to the insertion surface 1002 a distance X across the chassis 104. As the carriage moves parallel to the insertion surface 1002 the cam paths 506 interact with the carrier pins to transition the sharp carrier substantially perpendicular to the direction of the carriage. In FIG. 12B, the sharp carrier 110 is shown nearly fully displaced toward the insertion surface. The displacement of the sharp carrier 110 results in the sharp 108 being inserted below the insertion surface 1002.

In some embodiments the proximal end of the sensor assembly 106 is sandwiched between the carriage and the electronics module 114 so the sensor assembly is transitioned parallel to the insertion surface upon depressing the actuator 118. However, as the distal end of the sensor moves parallel to the insertion surface (generically, this direction can be referred to as horizontal) the distal end passes through the sensor aperture and encounters the sensor deflector 332. The sensor deflector 332 redirects the movement of the sensor assembly from parallel to the surface of insertion to substantially perpendicular to the surface of insertion. Additionally, having the sensor deflector 332 aligned with the sharp opening 328 results in the distal end of the sensor assembly being cooperatively inserted with the sharp. The example described above should not be construed as limiting. It should be recognized that in other embodiments the sensor deflector can be configured to redirect the sensor to angles other than substantially perpendicular to the insertion surface. In other embodiments, when the carriage is in the first position, there can be changes to the location of the distal end of the sensor relative to the sensor aperture. For example, when in the first position, the distal end of the sensor assembly can be within the sensor channel but outside of the sensor aperture or within the sensor aperture. One advantage of keeping the distal end of the sensor assembly outside of the sensor aperture would be minimizing potential rubbing between the sensor aperture and sensor assembly during transport and storage. Conversely, if the distal end were within the sensor aperture, there is decreased likelihood of the sensor not passing through the sensor aperture during the insertion process.

Figure 13A:
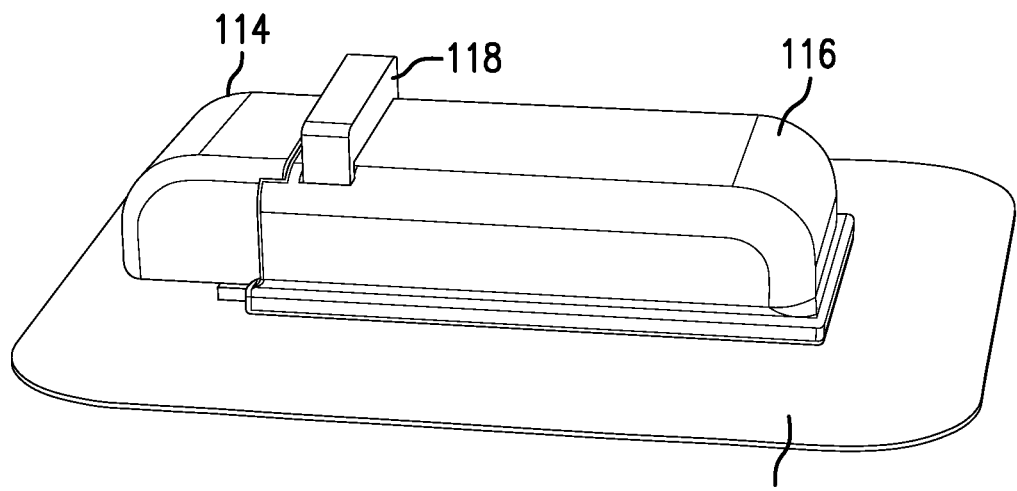
FIGS. 13A and 13B are a pseudo-isometric view and cross-sectional view of the on-body system in a second position.
Figure 13B:
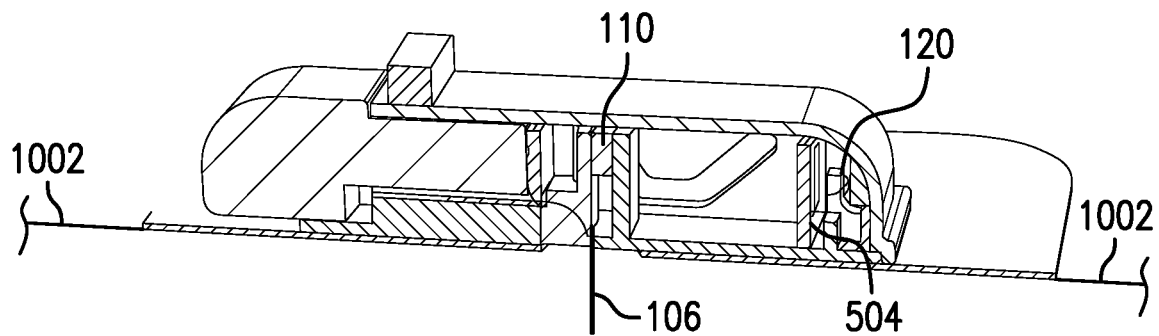

FIGS. 13A and 13B are a pseudo-isometric view and cross-sectional view of the on-body system in a second position, in accordance with embodiments of the present invention. With reference to FIG. 9, the exemplary illustrations in FIGS. 13A/13B coincide with completion of operation 908. In FIGS. 13A/13B energy storage 120 has been depleted and the carriage is in the second position. Accordingly, the sensor assembly has been inserted below the insertion surface 1002. The sharp carrier 110 has been raised so the sharp has returned to being above the insertion surface and the on-body system is ready to function for its intended lifespan.

The insertion technique illustrated in FIGS. 10A-13B is at least partially enabled by the mechanical properties of the sensor assembly. Even before insertion, when the sensor assembly is coupled to the carriage, the sensor assembly is deformed essentially 90 degrees. During insertion, the sensor deflector further deforms the distal end of the sensor assembly 90 degrees within fractions of a second. Both deformations of the sensor assembly require a sensor assembly with robust mechanical properties. Sensors based on rigid substrates or brittle coatings on wires may be wholly unsuitable for both prolonged deformation (attachment to the carriage) and rapid deformation (passing across the sensor deflector). Additionally, optimizing the overall thickness of the sensor assembly can be greatly beneficial during cooperative insertion. In many embodiments the overall thickness of the sensor assembly is between 0.002" and 0.020", with preferred embodiments having a thickness between 0.004" and 0.010". Even assuming a sensor based on a rigid substrate or coated wire could navigate the sensor deflector, the overall thickness of the sensor assembly and other mechanical properties may be incompatible with cooperative insertion. Specifically, the wound channel necessary to insert the sensor may require the use of a needle.

The mechanical properties of the sensor assembly further enable another distinguishing characteristic of the insertion technique. Specifically, the translation of the sensor assembly parallel to the insertion surface. Note that between the first position and the second position, the distal end of the sensor traverses both a horizontal distance and a vertical distance. However, between the same first position and second position, the proximal end traverses in substantially only the horizontal. Because of draft and other necessities of the manufacturing process, the proximal end of the sensor assembly traverses some miniscule vertical component between the first and second position. However, relative to the vertical displacement of the distal end, the vertical displacement of the proximal end is essentially negligible. This miniscule, negligible vertical displacement enables the on-body system to have a relatively low, compact profile considering that after insertion, all of the insertion hardware remains in place. Because typical insertion schemes require substantially equal displacement of both the distal and proximal ends of the sensor assembly, insertion mechanisms are generally large and somewhat cumbersome. Excessive mechanical complexity or unwielding size that often requires two hands to operate are common traits of insertion tools that do not take advantage of cooperative insertion. Without cooperative insertion, the insertion needle must carry the sensor to the insertion depth and also be withdrawn back into the insertion tool. Cooperative insertion, combined with horizontal displacement being translated into vertical displacement simplifies insertion of the on-body system which in turn minimizes the physical footprint and overall size of the on-body system. Commensurate with the reduced size of the on-body system is the ability to perform insertion with one hand which further enables insertion wherever a person can reach with one hand. The specific examples described above should are intended to be exemplary rather than limiting. Other embodiments include additional components or features that are described throughout this disclosure.

Figure 14A:
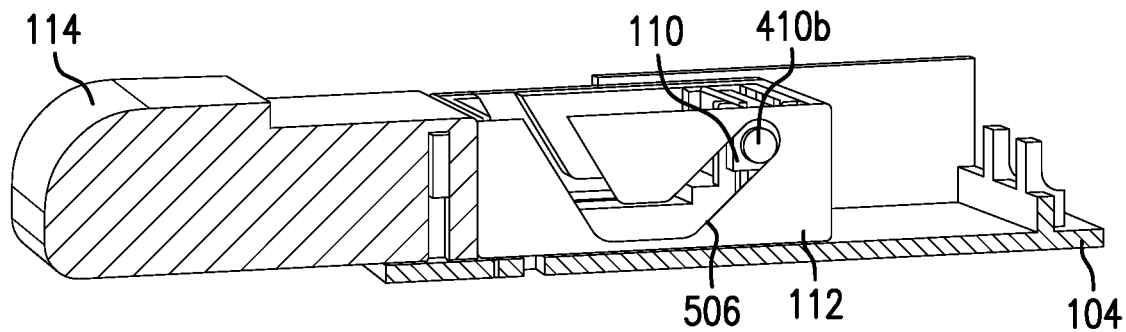
FIGS. 14A-14D are cross-sectional views of the on-body system as the carriage transitions from the first position to the second position.
Figure 14B:
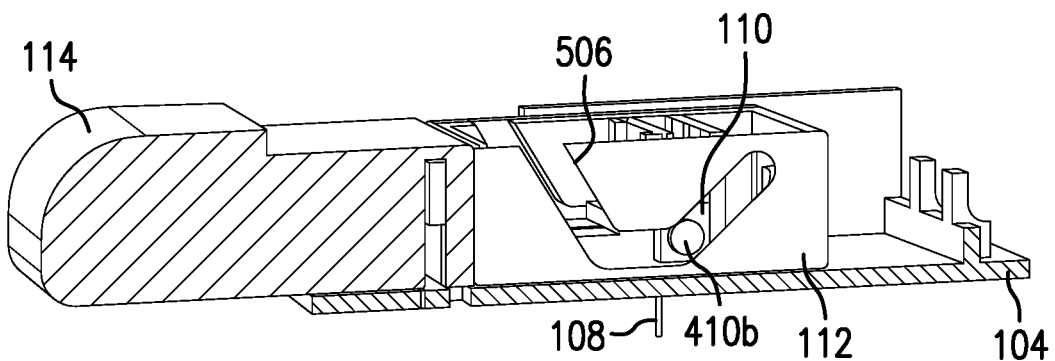
Figure 14C:
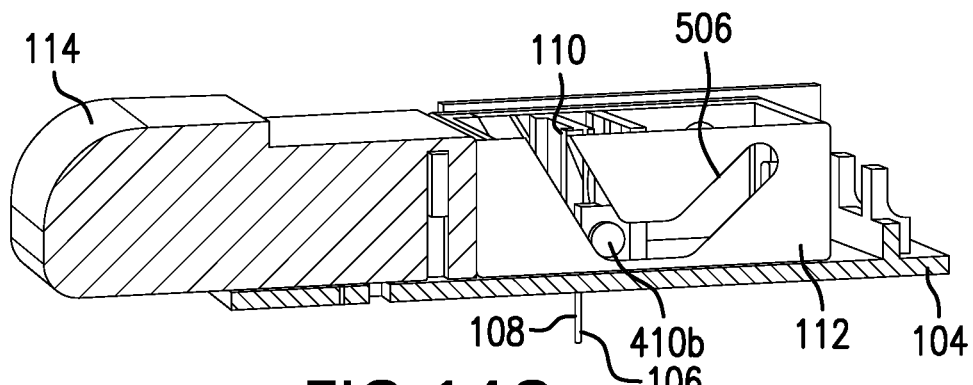

FIGS. 14A-14D are cross-sectional views of the on-body system as the carriage transitions from the first position to the second position, focusing on interactions between the sharp carrier and cam path, in accordance with embodiments of the present invention. FIG. 14A shows the relevant components at the first position. Within the cam path 506 is the carrier pin 410b supporting the sharp carrier 110 so the sharp 106 is not protruding through the sharp opening (not shown). FIGS. 14B and 14C show the relevant components as the carriage 112 and electronic components 114 transition from the first position to the second position. In FIG. 14B the cam path 506 drives the sharp carrier 110 toward the insertion surface resulting in the sharp 108 protruding through the sharp opening. In FIG. 14B the sharp 108 is illustrated at an insertion depth below the insertion surface.

Figure 14D:
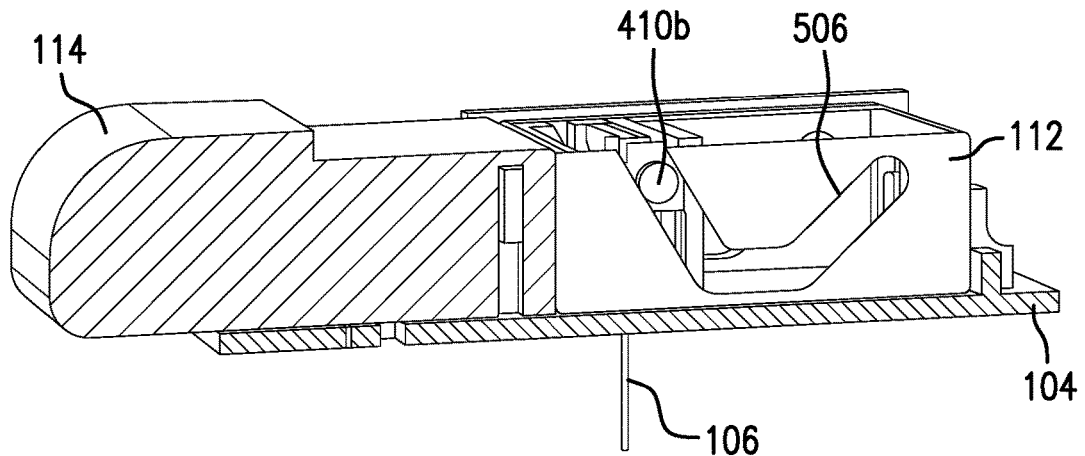

With FIG. 14C, the cam profile 506 maintains the sharp 108 at a depth below the insertion surface and the sensor assembly is shown being inserted to a depth that will eventually be further below the insertion surface than the sharp. The continued translation of the carriage 112 parallel to the insertion surface driving the sensor assembly 106 across the sensor deflector to be cooperatively inserted with the sharp. FIG. 14D shows the relevant components at the second position. The cam path 506 has retracted the sharp into the on-body system while the sensor 106 has reached the desired insertion depth.

In many embodiments the cam paths include features to make the on-body system sharp safe once the carriage is in the second position. Sharp safe is intended to mean that the carriage cannot accidentally be returned to the first position thereby deploying the sharp outside of the on-body system. In some embodiments the cam paths include lock out features such as profiles within the cam paths that nudge the sharp out of alignment with the sharp opening. Alternatively, one way snap features between the carriage and chassis can lock the entire carriage in the second position. Similarly, one way snap features between the carriage and the cover can lock the carriage in the second position. In other embodiments, one-way snap features associated with the electronics module interact with features on the cover or chassis to secure the on-body system in the second position. In embodiments where the on-body system is made sharp safe, recycling or reusing the electronics module is made possible by inclusion of systems that enable the carriage to be released from the second position once the on-body system is removed from the insertion surface. The particular embodiments discussed above should be viewed as exemplary. Other embodiments based on, or incorporating concepts discussed above may fall within the scope of this disclosure.

Modifications to the cam paths, sensor length, sensor deflector and other aspects of the on-body system design enable different timings and coincidence of insertion along with insertions depths for both the sharp and the sensor assembly. For example, different embodiments include the various permutations of having the sharp pierce the insertion surface prior to, substantially simultaneously, or before the sensor. Similarly, different embodiments includes the various permutations of having the insertion depth of the sharp be greater, substantially equal to, or less than the insertion depth of the sensor assembly.

Figure 15:
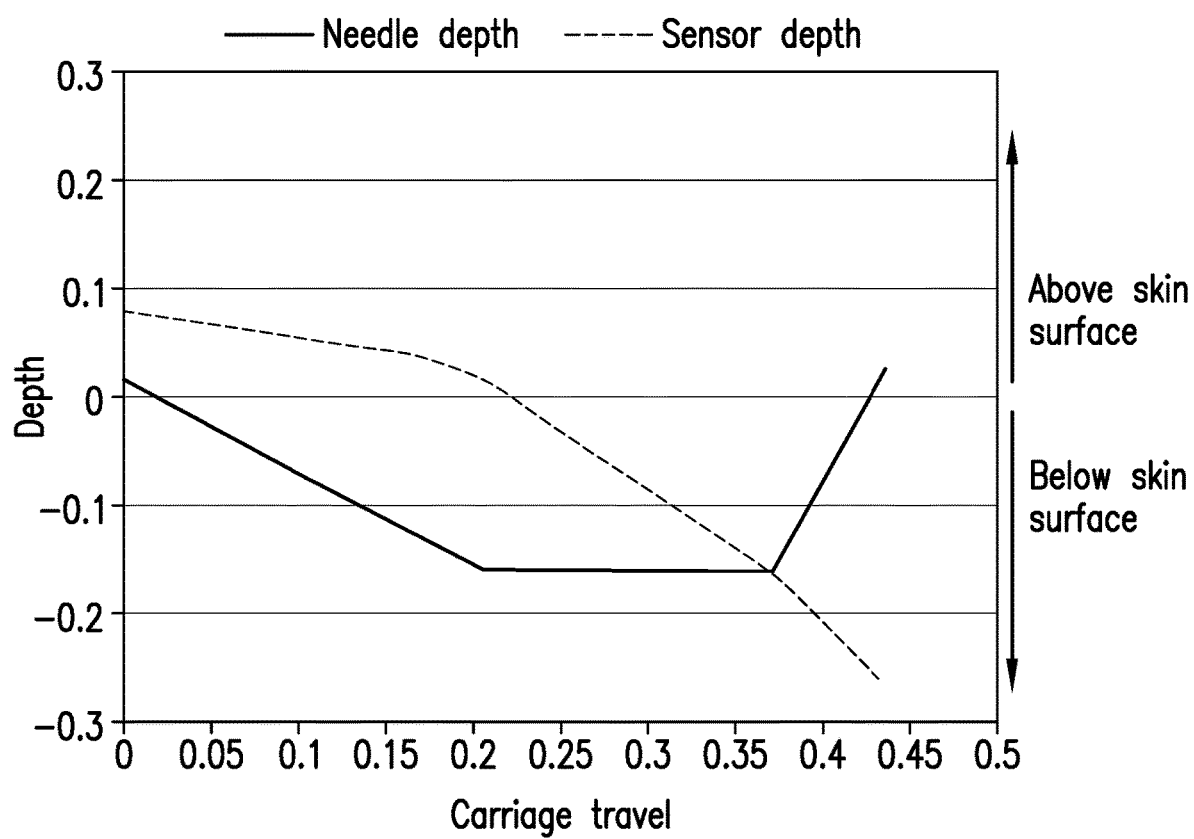
FIG. 15 is an exemplary plot that illustrates sharp depth and sensor insertion depth as the carriage traverses between the first position and the second position.

FIG. 15 is an exemplary plot that illustrates sharp depth and sensor insertion depth as the carriage traverses between the first position and the second position, in accordance with embodiments of the present invention. FIG. 15 illustrates a further benefit of cooperative insertion. Note that with cooperative insertion the sensor assembly continues to be inserted further beneath the insertion surface while the sharp is being drawn in an opposite direction, toward the insertion surface. Cooperative insertion uses a sensor assembly that is robust enough to continue insertion without assistance from the sharp. Using the sensor assembly alone during insertion reduces the wound channel and decreases tissue disruption and displacement. In some embodiments, reducing the wound channel enables reduced run-in times for the sensor assembly. In other embodiments, reducing the wound channel promotes increased sensor longevity by minimizing a response from the immune system. The embodiment illustrated in FIG. 15 is exemplary and wound generation resulting from cooperative insertion can be controlled, modulated or even minimized by manipulating various aspects of insertion such as the sharp depth, sharp width, sensor insertion depth and the translational speed of the carriage.

Figure 16:
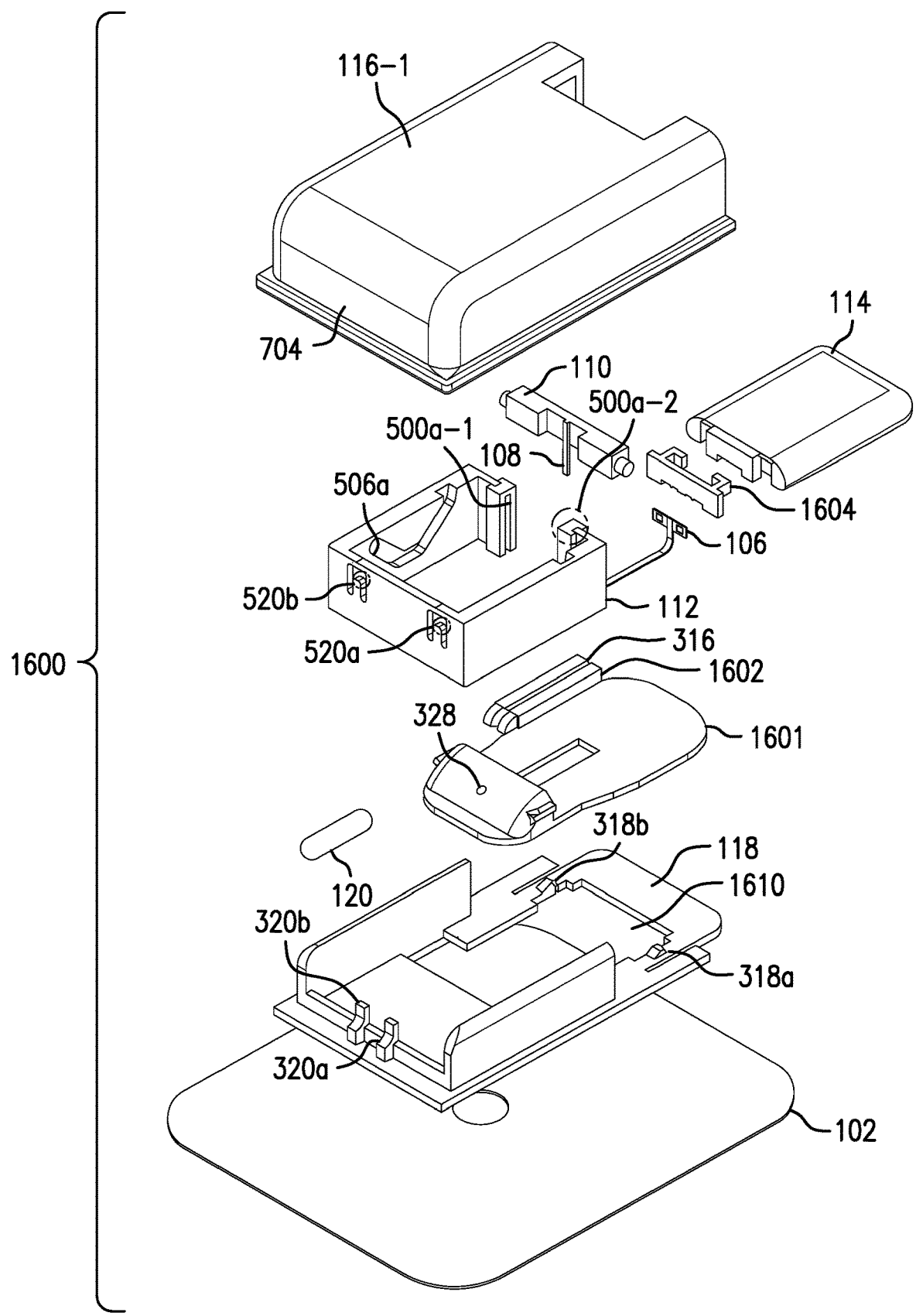
FIG. 16 is a two-piece on-body system with a removable insertion device and a lower profile electronics module.

FIG. 16 is a two-piece on-body system 1600 with a removable insertion device and a lower profile electronics module 114-1, in accordance with the present invention. Whereas the entirety of the on-body system 100 was intended to remain attached to the insertion surface, the two-piece on-body system 1600 includes a detachable insertion aid or insertion device. In use, after insertion if completed, the insertion aid is removed and what remains on-body has a smaller footprint and overall volume compared to on-body system 100. While on-body system 100 may be preferred for simplicity, it can be beneficial to provide options, particularly options that reduce the visibility of ambulatory medical devices.

The exemplary two-piece on-body system 1600 includes the patch 102 and a chassis 104-1. The illustration of the chassis 104-1 includes an actuator 118 that is integrated with the chassis 104-1 rather than the previously discussed separate actuator 118 and chassis 104 (FIG. 1). While the actuator 118 may have been integrated with the chassis 104-1, common features between chassis 104-1 and 104 includes anchors 320a/320b and carriage retainers 318a/318b. Additionally, in other embodiments the integrated actuator 118 of chassis 104-1 can be adapted for use with chassis 104. The actuator 118 is intended to be exemplary and may include different physical embodiments, such as but not limited to, a single piece (e.g. a button or a slide) or multiple pieces (e.g. two buttons squeezed between thumb and forefinger). Additionally, the different physical embodiments of the actuator 118 may implement single or multiple actuation movements that include, but are not limited to, pushing/pressing, sliding, lifting, squeezing and twisting. Because the chassis 104-1 is intended to be removed after insertion, adhesive no longer couples the chassis 104-1 to the patch 102. Another difference between the chassis 104-1 and chassis 104 is the inclusion of chassis opening 1610 that accommodates a base 1601.

The base 1601 is coupled to the patch 102 and forms the foundation of what remains on-body for the two-piece on-body system 1600. The base 1601 includes sharp opening 328 that allows the sharp to pass through the base and be inserted into the insertion surface. A sensor guide 1602 is coupled with the base 1601. The sensor guide 1602 includes the sensor channel 316. In some embodiments the base 1601 and the sensor guide 1602 are integrated into a single piece. In many of the single piece embodiments, portions of the base 1601 are made from soft touch plastics that are overmolded onto more rigid plastics that form the sensor channel 316 and features like the sensor deflector (not shown), also found within the base 1601.

In the two-piece on-body system 1600, the carriage 112 retains features like the attach points 520a/520b and cam paths 506a/506b. However, with the two-piece on-body system 1600, retainers 500a-1 and 500b-2 are used to couple a sensor carrier 1604 to the carriage 112. Recall with the on-body system 100 the retainers of the carriage were directly coupled to the electronic module. The sensor carrier 1604 includes a sensor block where the proximal end of the sensor assembly 106 is secured to the sensor carrier 1604. The sensor carrier 1604 further includes electronic retainers 1612a/1612b that are intended to couple the electronics module 114 to the sensor carrier 1604.

The sharp 108 is coupled to the sharp carrier 110 that still has carrier pins 410a/410b. While not visible in FIG. 16, the cover 116-1 includes the first guide 312 and the second guide 314 that constrain the sharp carrier 110 to substantially vertical movement as the carrier pins 410a/410b follow the cam paths 506a/506b. For simplicity, energy storage 120 remains illustrated as a rubber band. However, as previously discussed, various embodiments can use different techniques to store energy. The components illustrated and described in FIG. 16 should be construed as exemplary rather than limiting. Discrete components may be combined and multifunction parts may be separated into discrete components and still fall within the scope of this disclosure. This is made evident by the combined actuator 118 and chassis 104 found in the two-piece on-body system 1600 compared to the discrete actuator 118 and chassis used with the on-body system 100.

Figure 17A:
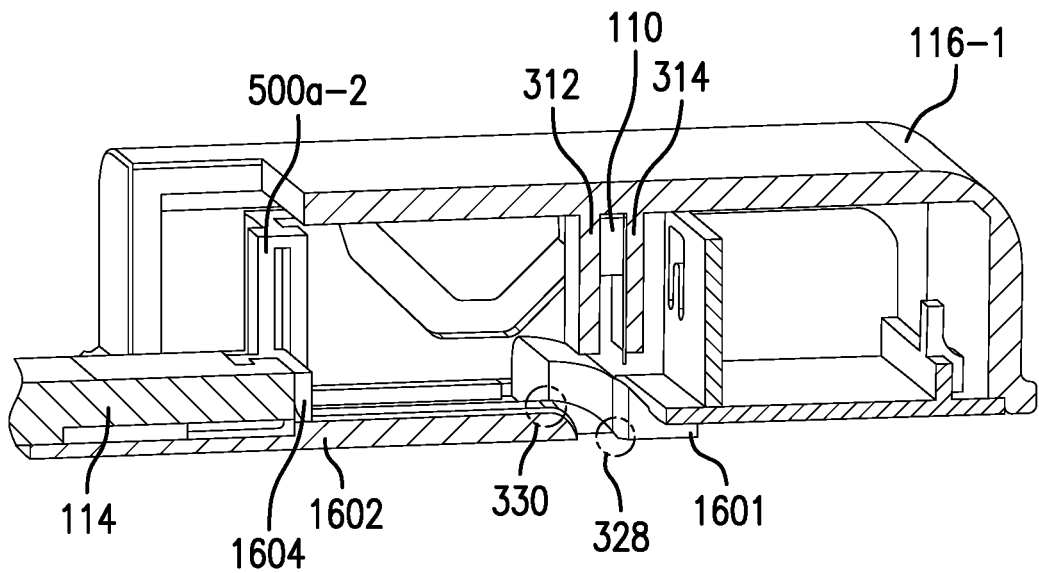
FIGS. 17A and 17B are section views of the two-piece on-body system.
Figure 17B:
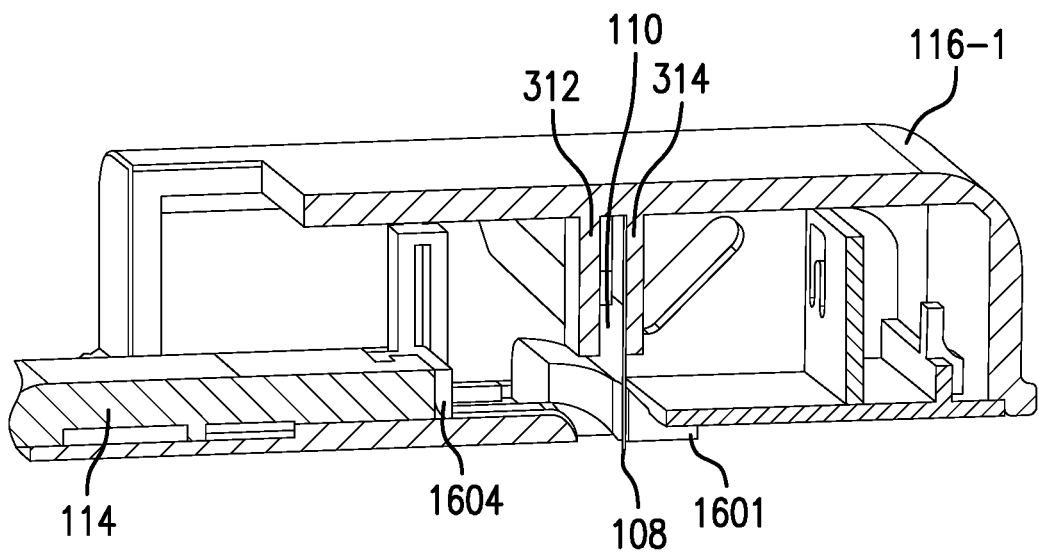

FIGS. 17A and 17B are cross-section views of the two-piece on-body system 1600 in accordance with embodiments of the present invention. FIG. 17A is an exemplary illustration of the two-piece on-body system 1600 prior to activation of the actuator. FIG. 17B is an exemplary illustration of the two-piece on-body system 1600 as the sensor carrier drives the sharp 108 through the sharp opening 228. In each FIGS. 17A/17B, the cross-section view provides insight on the interaction between the sensor carrier, the sensor guide, the carriage, the base and the electronics module. Additional insight can be gained into how the first guide and second guide, incorporated into the cover 116-1 interacts with the sharp carrier 110. Likewise visible in both FIGS. 17A and 17B are embodiments of the sensor aperture and sharp opening. While the embodiment may be different than the on-body system 100 previously discussed, the operation and interaction of the individual components remains somewhat consistent. The carriage is released from a first position and translates in a direction parallel to the insertion surface. The translation of the carriage moves the proximal end of the sensor assembly parallel to the insertion surface while the distal end of the sensor assembly is transitioned to movement substantially perpendicular to the insertion surface by the sensor deflector. In each embodiment, the distal end of the sensor is cooperatively insertion with the sharp, whose vertical movement is imparted by cams formed in the carriage that interact with pins on the sharp carrier.

Figure 18A:
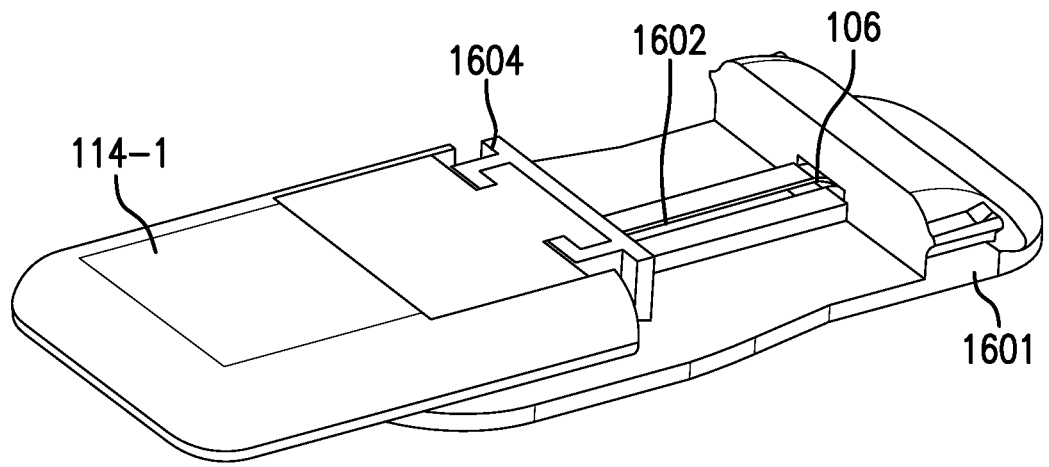
FIGS. 18A and 18B are pseudo-isometric views of the components that remain after insertion.
Figure 18B:
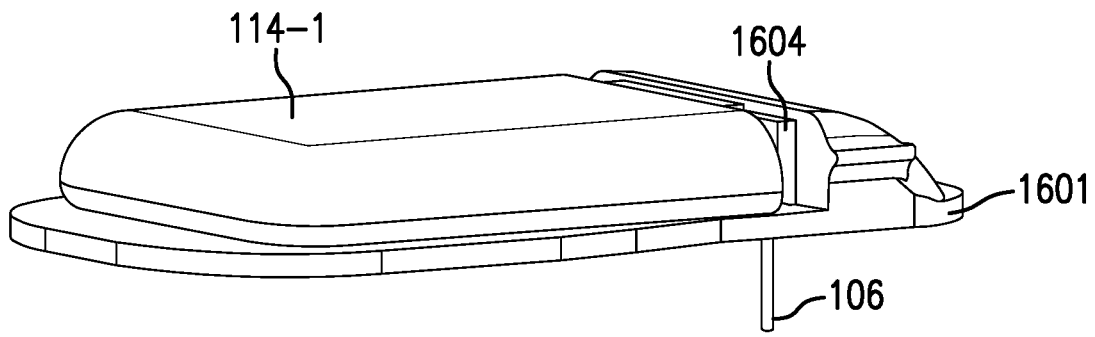

FIGS. 18A and 18B are pseudo-isometric views of the components that remain after insertion, in accordance with embodiments of the present invention. FIGS. 18A and 18B show the components that remain on-body, or the remainder components, are the base 1601, the sensor guide 1602, the sensor carrier 1604, the electronics module 114-1 and the sensor assembly 106. FIG. 18A is an exemplary illustration of the remainder components without the presence of the other insertion aid components, prior to insertion. FIG. 18B shows an exemplary illustration of the remainder components after insertion has been completed, as evidence by the sensor assembly 106 being visible beneath the base.

Figure 19A:
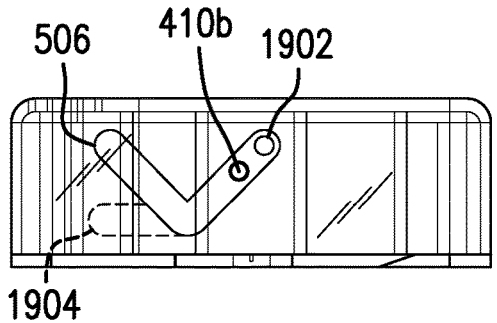
FIGS. 19A-19F illustrate an alternative embodiment of cooperative insertion.

FIGS. 19A-19F illustrate an alternative embodiment of cooperative insertion, in accordance with embodiments of the present invention. With previously discussed embodiments of cooperative insertion the sensor was being displaced substantially parallel to the insertion surface and the sensor deflector transitioned or deformed the sensor from substantially horizontal to substantially vertical. In the embodiment shown in FIGS. 19A-19F, the sensor assembly is displaced vertically by the cam system previously used to move the sharp. Throughout FIGS. 19A-19F, the sharp carrier pin 410b is shown in cam path 506. Also within the cam path 506 is sensor carrier pin 1902. In FIG. 19A, the sharp carrier pin 410b and sensor carrier pin 1902 are shown in the first position.

Figure 19B:
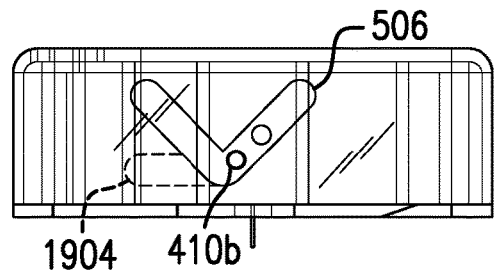
Figure 19C:
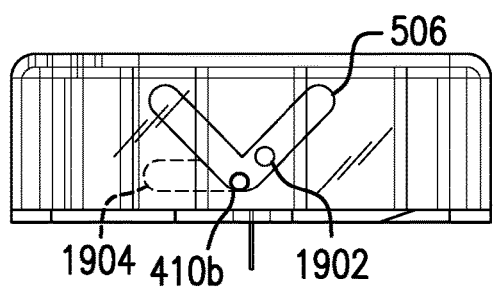
Figure 19D:
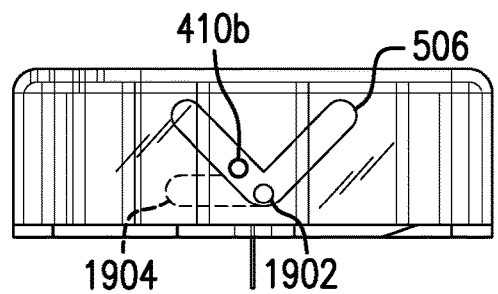
Figure 19E:
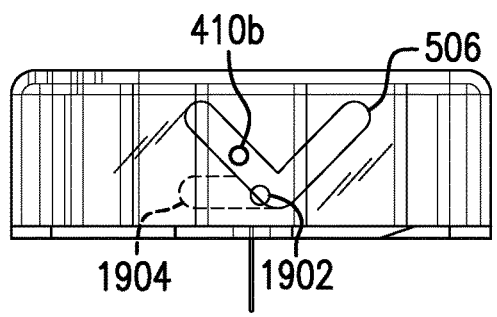
Figure 19F:
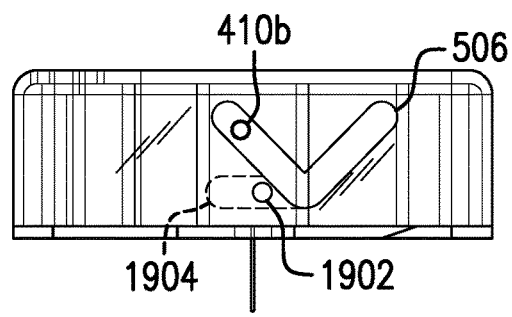

In FIG. 19B, the carriage has begun transitioning between the first position and the second position. The sharp carrier pin 410b confined with the cam path 506 moves the sharp vertically toward the insertion surface. Likewise the sensor carrier 1902 moves the sensor toward the insertion surface. FIG. 19C illustrates the sharp carrier pin 1902 at bottom of the cam path 506 and the sensor carrier pin following behind. Also visible is a spur cam path 1904. The spur cam path 1904 is sized to prevent the sharp carrier pin from entering the spur cam path 1904. However, the spur cam path 1904 is sized so the sensor carrier pin 1902 will be guided into the spur cam path 1904. FIG. 19D illustrates retraction of the sharp carrier 410b via the cam path 506 and the maximum insertion depth of the sensor. FIGS. 19E and 19F further illustrate retraction of the sharp and the sensor carrier pin 1902 going into the spur cam path 1904, thereby keeping the sensor inserted at its maximum insertion depth.

The alternate embodiments of cooperative insertion discussed above can be implemented with either a durable or disposable on-body system with slight modifications to other parts such as the chassis and/or cover. Additionally, use of the alternative embodiments of cooperative insertion may require alternative electrical connection techniques or schemes. However, note that once modifications are made to accommodate the sensor carrier within the cam path, all embodiments of cooperative insertion can implement minimal insertion of the sharp as the mechanical properties of the sensor can sustain insertion to the desired depth beneath the insertion surface.

In the discussion of both the on-body system 100 and the two-piece on-body system 1600, activation of the actuator release stored energy to translate the carriage from the first position to the second position. In alternative embodiments, energy storage is eliminated resulting in insertion being performed manually. In embodiments of manual insertion the transition from the first position to the second position is achieved by manually applying force to the electronics module after it has been connected to the carriage. In preferred embodiments of manual insertion, a pinching movement between a thumb and other digit is used to translate or transition the electronics module from the first position to the second position.

One benefit to removing the energy storage system is simplification of the manufacturing process for the on-body system. Another rationale for removing the energy storage system is to increase the shelf-life of the on-body systems. Depending on the implementation of the energy storage system, keeping the energy storage system charged or loaded for prolonged periods may compromise the translation speed of the carriage. With manual insertion or stored energy assisted insertion, both on-body system 100 and on-body system 1600 enable ambidextrous one-handed insertion. Ambidextrous one-handed insertion can be beneficial to a user because it allows placement of the on-body device in areas generally unavailable to a person without a second person to assist with insertion. For example, with ambidextrous one-handed insertion a single individual can place the on-body system on the back of an upper arm or the small of their back. With alternative products that require two hands to achieve insertion, it may be extremely difficult if not outright impossible to reach similar areas to insert the sensor.

A manual insertion embodiment can find additional application within veterinary medicine and animal husbandry fields. Insertion aids or tools that utilize energy storage systems that generate a pronounced activation impulse or grating mechanical sounds like those produced by mechanical springs, can startle or spook animals under veterinary care. Because the manually operated on-body system can be quieter, there may be less likelihood to startle or spook animals while inserting the sensor. This not only enables monitoring of physiological characteristics of the animals, but also can improve the safety of technicians or owners that insert the sensor. Furthermore, in addition to being used within a clinical veterinary environment, embodiments of the on-body system can be used to monitor each or individual animals within a herd enabling the on-body system to have applications for animal husbandry. For example, particular analytes in combination with physiologic conditions can be monitored in real-time to assist in determining characteristics such as, but not limited to stress, overall animal health, fertility, hydration, activity and the like. While veterinary embodiments have been generally discussed in conjunction with manual insertion, other embodiments utilizing stored energy to achieve insertion can also be used with veterinary applications.

An alternate embodiment also enables extended shelf life while using stored energy to assist with insertion. Previously discussed energy assisted embodiments have the carriage in the first position, where the energy system is loaded and ready to release. In alternate embodiments manufacturing, storage and shipment of the on-body system is done with the carriage in the second position. In some embodiments, removing the on-body system from the packaging automatically transitions the carriage to the first position. In other embodiments, a user must manually transition the carriage from the second position to the first position by "arming" the on-body system.

Figure 20A:
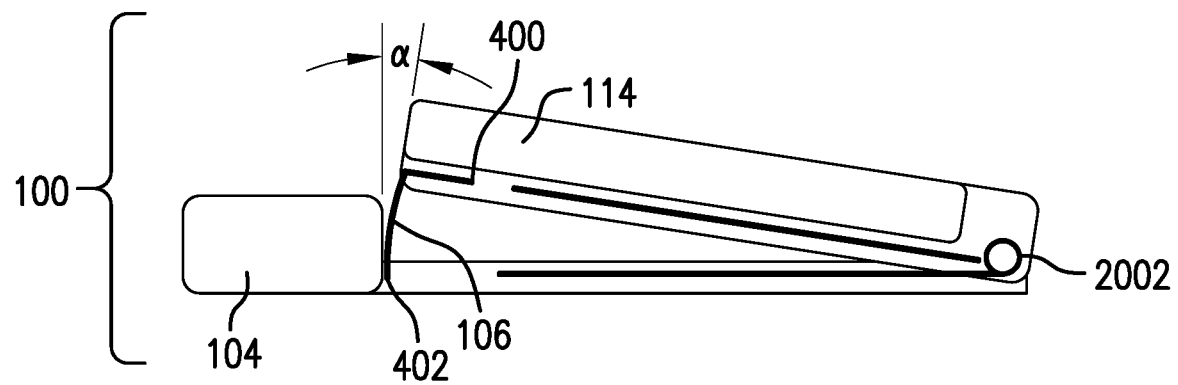
FIGS. 20A and 20B are an exemplary illustration of an alternative embodiment of insertion.
Figure 20B:
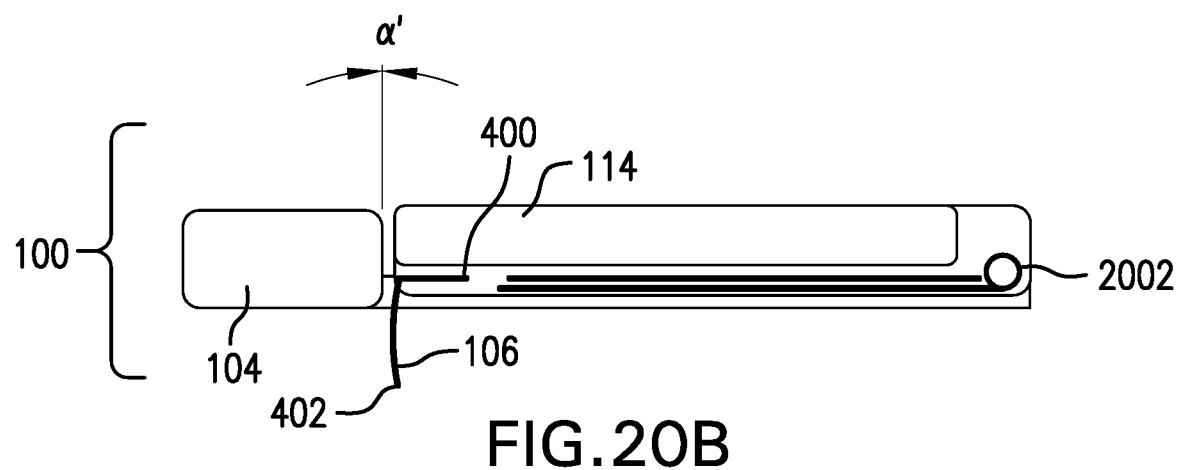

FIGS. 20A and 20B are an exemplary illustration of an alternative embodiment of insertion, in accordance with embodiments of the present invention. Previously described embodiments have the proximal end moving substantially, if not entirely parallel to the insertion surface. In other embodiments, the translation of the proximal end of the sensor may include both horizontal (parallel to the insertion surface) and vertical (perpendicular to the insertion surface) components. For example, FIG. 20A shows an alternate embodiment of an on-body system 100 in a first position where the sensor assembly 106 forms a first angle α between the chassis and the electronics module 114. FIG. 20B is an exemplary illustration of the on-body system 100 in a second position after insertion of the sensor assembly 106 where the angle α' is different than when the on-body system is in the first position. Note that between FIGS. 20A and 20B the proximal end of the sensor assembly 400 traversed a vertical component and a horizontal component. The embodiments illustrated in FIGS. 20A and 20B may optionally include a sharp that promoted previously discussed aspects of cooperative insertion. An additional benefit of cooperative insertion, enabled by the immediate embodiment along with the previously discussed embodiments is reducing the likelihood of bodily fluid spatter during insertion because of the reduced amount of energy being applied during insertion.

While the description above refers to particular embodiments of the present invention, it will be understood that many modifications may be made without departing from the spirit thereof. It is intended that the various embodiments of an on-body system described above can be interchangeably reconfigured with each other where possible to create a wide array of on-body systems. The various on-body systems are intended to utilize various aspects of the simplified insertion systems disclosed above such as cooperative insertion, translation of the proximal end of the sensor parallel to the insertion surface, powering the sensor before insertion, and where appropriate, retention of the entire on-body system for an intended wear-period where the on-body system is sharp-safe.

Furthermore, embodiments specifying use of an analyte sensor should not be considered limiting. Specifically, this disclosure is intended to encompass embodiments utilizing sensors capable of cooperative insertion that measure individual or multiple physical parameters such as, but not limited to, concentrations of analytes, temperature, perfusion, pressure, and impedance. The disclosure is being made without being bound by any particular sensor technology or theory of operation and should be construed to encompass insertion of sensors within subcutaneous tissue along with alternative implant sites such as the vasculature and organs (both percutaneously, and organs exposed during surgery). Accordingly, the disclosed embodiments and associated theories of operation are intended to be considered in all respects as illustrative and not restrictive.

The invention claimed is:

1. An on-body insertion system, comprising:
    a sensor having a proximal end and a distal end, wherein, in a first position, the proximal end and the distal end are substantially parallel to an insertion surface;
    an actuator;
    a sharp substantially perpendicular to the insertion surface;
    a stationary deflector surface,
    wherein the sensor is configured to create its own wound channel,
    wherein the on-body insertion system is configured such that activation of the actuator transitions the sensor to a second position and, during the transition, imparts movement of the sensor in a direction substantially parallel to the insertion surface, the movement causing the distal end to contact the stationary deflector surface,
    wherein the transition includes substantially vertical movement of the sharp throughout the transition and negligible vertical movement of the proximal end throughout the transition, and
    wherein the transition further includes cooperative insertion of the sensor and the sharp to place the distal end beneath the insertion surface.

2. The on-body insertion system described in claim 1, wherein the sharp is fully contained within the on-body insertion system in the first position, the transition to the second position inserting the sharp to a sharp depth beneath the insertion surface and retracting the sharp within the on-body insertion system.

3. The on-body insertion system described in claim 2, wherein the sharp and sensor contact the insertion surface simultaneously.

4. The on-body insertion system described in claim 2, wherein the on-body insertion system is further configured such that the sharp contacts the insertion surface before the sensor.

5. The on-body insertion system described in claim 2, wherein the on-body insertion system is further configured such that the sensor contacts the insertion surface before the sharp.

6. The on-body insertion system described in claim 2, wherein the on-body insertion system is further configured such that the distal end of the sensor is inserted to a sensor depth, the sensor depth being further beneath the insertion surface than the sharp depth.

7. The on-body insertion system described in claim 2, wherein the on-body insertion system is further configured such that the distal end of the sensor is inserted to a sensor depth, the sensor depth being and sharp depth being substantially similar depths beneath the insertion surface.

8. The on-body insertion system described in claim 2, wherein the on-body insertion system is further configured such that the distal end of the sensor is inserted to a sensor depth, the sharp depth being further beneath the insertion surface than the sensor depth.

9. The on-body insertion system described in claim 2, wherein the on-body insertion system is further configured such that while the sharp is being retracted, the sensor is being inserted to the sensor depth.

10. The on-body insertion system described in claim 1, wherein the on-body insertion system is further configured such that prior to activation of the actuator, electrical power is supplied to the sensor.

11. The on-body insertion system described in claim 2, wherein the on-body insertion system is sharp safe when the sensor is in the second position.

12. The on-body insertion system described in claim 1, wherein other than adhesive liners, an entirety of the on-body insertion system is configured to remain coupled to the insertion surface for an intended wear-period.

13. The on-body insertion system described in claim 1, wherein the on-body insertion system is defined by two pieces, a first piece being an insertion aid and a second piece, after the sensor is in the second position, the second piece remaining coupled to the insertion surface while the first piece is detached.

14. The on-body insertion system described in claim 1, wherein activation of the actuator releases stored energy, the released stored energy transitioning the sensor from the first position to the second position.

15. The on-body insertion system described in claim 1, wherein the on-body insertion system is further configured such that activation of the actuator overcomes a detent, the activation being a pinching movement between thumb and another digit that transitions the sensor from the first position of the second position.

16. A method of inserting a sensor assembly, comprising:
    activating an actuator to release the sensor assembly from a first position,
    the sensor assembly having a proximal end, a distal end, wherein, in the first position, the proximal end and the distal end are substantially parallel to an insertion surface, wherein the sensor assembly is configured to create its own wound channel;
    traversing a proximal end of the sensor assembly from the first position to a second position, the traversing involving negligible vertical movement of the proximal end, the traversing further being substantially parallel to the insertion surface;
    wherein a distal end of the sensor assembly interacts with a stationary deflector and a sharp to become inserted below the insertion surface when the proximal end of the sensor assembly is in the second position, the sharp moving substantially vertically while the sensor assembly traverses between the first position and the second position; and
    inserting the sensor beneath an insertion surface via cooperative insertion of the sharp and sensor assembly.

17. The method of inserting a sensor assembly described in claim 16, wherein the cooperative insertion comprises the sharp assisting in inserting the sensor assembly.

18. The method of inserting a sensor assembly described in claim 17, wherein inserting the sensor beneath an insertion surface further comprises the distal end of the sensor assembly being inserted below the insertion surface further than the sharp.

19. The method of inserting a sensor assembly described in claim 17, further comprising withdrawing the sharp while the distal end of the sensor assembly continues to be inserted below the insertion surface.

20. The method of inserting a sensor assembly described in claim 16, further comprising supplying electrical power to the sensor assembly before activating the actuator.

\* \* \* \* \*